United States Patent
Reising et al.

(10) Patent No.: US 8,454,359 B2
(45) Date of Patent: *Jun. 4, 2013

(54) METHOD OF FORMING AN ORTHODONTIC TRANSFER TRAY

(75) Inventors: Brian C. Reising, Atlanta, GA (US); Giorgos Hatzilias, Buford, GA (US)

(73) Assignee: Brian C. Reising, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/484,764

(22) Filed: May 31, 2012

(65) Prior Publication Data

US 2012/0251969 A1    Oct. 4, 2012

Related U.S. Application Data

(60) Division of application No. 11/566,934, filed on Dec. 5, 2006, now Pat. No. 8,251,699, which is a continuation-in-part of application No. 10/750,194, filed on Dec. 31, 2003, now abandoned, and a continuation-in-part of application No. 10/749,918, filed on Dec. 31, 2003, now abandoned.

(60) Provisional application No. 60/742,311, filed on Dec. 5, 2005, provisional application No. 60/437,546, filed on Dec. 31, 2002.

(51) Int. Cl.
    *A61C 3/00* (2006.01)

(52) U.S. Cl.
    USPC .................................................. 433/24

(58) Field of Classification Search
    USPC ........................................ 433/3–24
    See application file for complete search history.

(56) References Cited

U.S. PATENT DOCUMENTS

| | | | |
|---|---|---|---|
| 3,906,634 | A | 9/1975 | Aspel |
| 3,949,477 | A | 4/1976 | Cohen et al. |
| 3,953,132 | A | 4/1976 | Michelsen |
| 4,001,940 | A | 1/1977 | Cusato |
| 4,083,114 | A | 4/1978 | Acevedo |
| 4,354,833 | A | 10/1982 | Fujita |
| 4,533,320 | A | 8/1985 | Piekarsky |

(Continued)

OTHER PUBLICATIONS

Ciuffolo et al., "Rapid prototyping: A new method of preparing trays for indirect bonding," American Journal of Orthodontics & Dentofacial Orthopedics, vol. 129, No. 1, Jan. 2006, 4 pgs.

(Continued)

*Primary Examiner* — Sunil K Singh
(74) *Attorney, Agent, or Firm* — Gardner Groff Greenwald & Villanueva, P.C.

(57) ABSTRACT

An orthodontic bracket having an opening for receiving a wire, but without a base to create a lever arm when the bracket is oriented in free space at a customized angle relative to a tooth surface. The bracket can be embedded into or encapsulated by an adhesive that is bonded to the tooth. A clip is provided for holding the bracket in position and occluding the opening while the adhesive is applied. And indirect methods of attaching the brackets to teeth are provided wherein the brackets can be attached to the lingual side of the teeth in a low-profile arrangement. A first method includes the step of positioning the brackets on a physical model of the teeth by using a positioning machine. A second method includes the step of positioning virtual brackets on a virtual model of the teeth using software, then generating a physical transfer try using rapid prototyping.

19 Claims, 19 Drawing Sheets

U.S. PATENT DOCUMENTS

| | | | |
|---|---|---|---|
| 4,712,999 | A | 12/1987 | Rosenberg |
| 4,749,352 | A | 6/1988 | Nicholson |
| 4,812,118 | A | 3/1989 | Creekmore |
| 4,927,362 | A | 5/1990 | Snead |
| 4,952,142 | A | 8/1990 | Nicholson |
| 5,230,620 | A | 7/1993 | Watanabe |
| 5,616,026 | A | 4/1997 | Cash |
| 5,820,370 | A | 10/1998 | Allesee et al. |
| 5,971,754 | A | 10/1999 | Sondhi et al. |
| 6,099,314 | A | 8/2000 | Kopelman et al. |
| 6,110,409 | A | 8/2000 | Allanic et al. |
| 6,120,287 | A | 9/2000 | Chen |
| 6,146,487 | A | 11/2000 | Lee et al. |
| 6,159,411 | A | 12/2000 | Kulkarni |
| 6,261,077 | B1 | 7/2001 | Bishop et al. |
| 6,264,468 | B1 | 7/2001 | Takemoto |
| 6,299,438 | B1 | 10/2001 | Sahagian et al. |
| 6,575,740 | B2 | 6/2003 | Kyung |
| 6,599,125 | B1 | 7/2003 | Freilich et al. |
| 6,664,986 | B1 | 12/2003 | Kopelman et al. |
| 6,739,869 | B1 | 5/2004 | Taub et al. |
| 6,776,614 | B2 | 8/2004 | Wiechmann et al. |
| 6,928,733 | B2 | 8/2005 | Rubbert et al. |
| 7,037,111 | B2 | 5/2006 | Miller |
| 7,128,866 | B1 | 10/2006 | Henningsen |
| 7,347,688 | B2 | 3/2008 | Kopelman et al. |
| 2001/0029007 | A1 * | 10/2001 | Abels .............................. 433/10 |
| 2001/0038991 | A1 | 11/2001 | Nicola et al. |
| 2003/0160784 | A1 | 8/2003 | Kopelman et al. |
| 2004/0073417 | A1 * | 4/2004 | Rubbert et al. ................. 703/11 |
| 2004/0157184 | A1 | 8/2004 | Reising |
| 2005/0003324 | A1 | 1/2005 | Reising |
| 2005/0158686 | A1 | 7/2005 | Wiechmann et al. |
| 2005/0191594 | A1 | 9/2005 | Taub et al. |
| 2006/0158665 | A1 | 7/2006 | Babyoff et al. |
| 2006/0212260 | A1 | 9/2006 | Kopelman et al. |
| 2008/0248437 | A1 | 10/2008 | Marshall |

OTHER PUBLICATIONS

International Search Report for PCT/US06/46427. Dated Sep. 25, 2007. 3 pgs.

Lingual Brackets, SDS Ormco Sybron Dental Specialties, 2 pgs.

Mayhew, Michael, "OrthoCAD iQ," OrthoCAD: Digital Technology Improving Orthodontic Practice, Nov. 11, 2006, 7 pgs. <http://www.orthocad.com/services/indirect_bonding.htm>.

Melsen et al., "The Ray Set: A New Technique for Precise Indirect Bonding," JCO, vol. 36, No. 11, Nov. 2002, 7pgs.

* cited by examiner

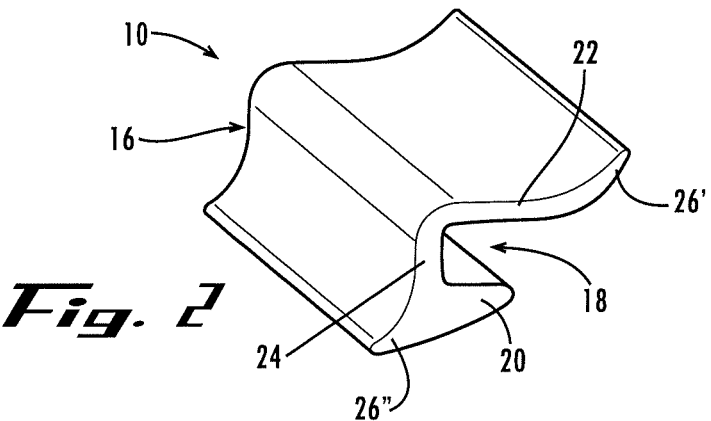
Fig. 2
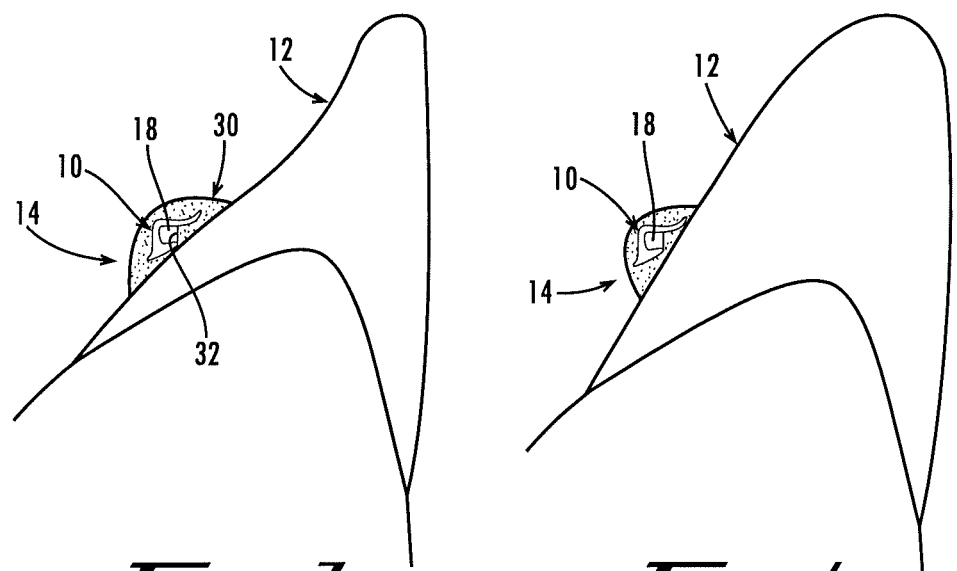
Fig. 3      Fig. 4
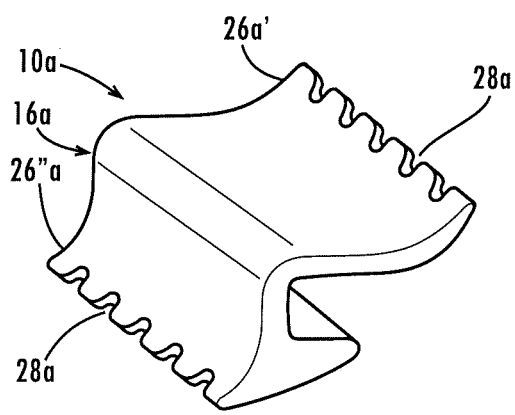   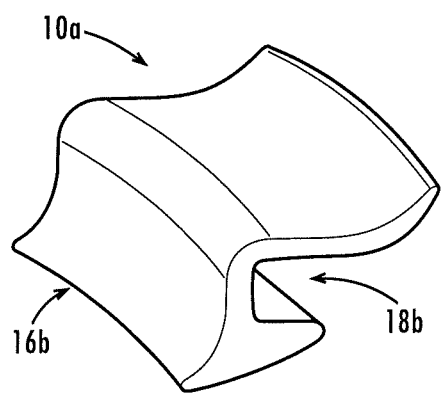
Fig. 5A      Fig. 5B

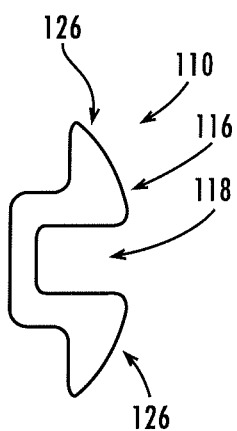
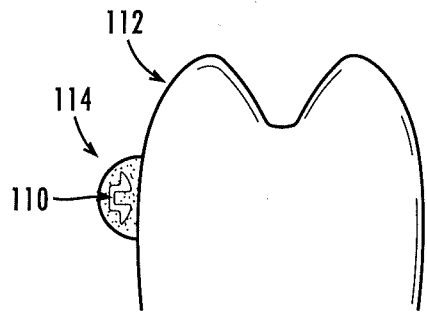
Fig. 6
Fig. 7
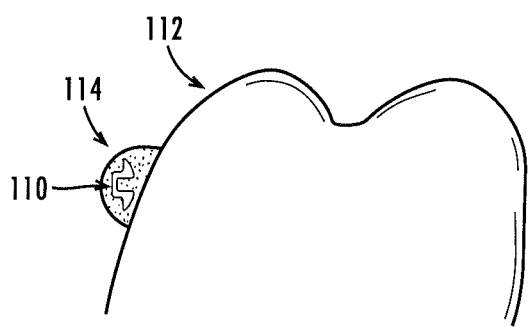
Fig. 8
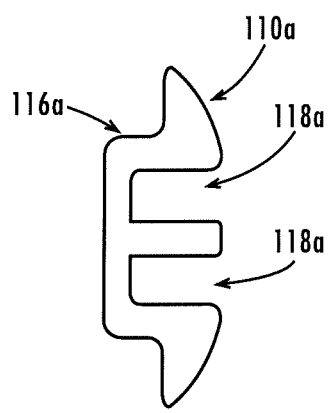
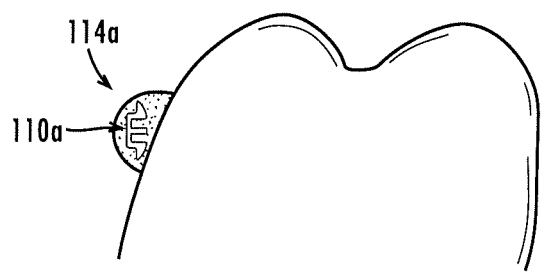
Fig. 9
Fig. 10

METHOD OF FORMING AN ORTHODONTIC TRANSFER TRAY

CROSS-REFERENCE TO RELATED APPLICATION

This application is a continuation-in-part of U.S. patent application Ser. No. 10/749,918, filed Dec. 31, 2003, and U.S. patent application Ser. No. 10/10/750,194, filed Dec. 31, 2003, both of which claim the priority benefit of U.S. Provisional Patent Application Ser. No. 60/437,546, filed Dec. 31, 2002, and this application claims the priority benefit of U.S. Provisional Patent Application Ser. No. 60/742,311, filed Dec. 5, 2005, which in their entirety are herein incorporated by reference.

TECHNICAL FIELD

The present invention relates generally to dentistry and orthodontics and, in particular, to attaching orthodontic brackets to teeth for repositioning the teeth.

BACKGROUND OF THE INVENTION

Orthodontists commonly correct the position of mal-occluded and mal-aligned teeth by therapeutic tooth movement. Therapeutic tooth movement is accomplished by the application of force to teeth to reposition them. Many orthodontic appliances have been used to apply force to teeth. The most commonly used orthodontic appliance for tooth movement is commonly known as the "edgewise appliance" or more specifically the "fixed pre-adjusted edgewise appliance"—also known as the "straight-wire appliance." The name "edgewise" refers to the general mechanism of a rectangular slot engaged by a force-generating rectangular wire. The terms "straight-wire", "pre-adjusted", and "pre-programmed" refer to an elective, though highly desirable, feature of an edgewise appliance system that will be described as follows.

An edgewise appliance system is a combination of many individual pieces designed to function in a coordinated fashion. The two primary components are tooth "attachments" that are attached to the teeth and "arch-wires" that engage the attachments. The attachments (brackets or bands) are semi-permanently and rigidly attached to the teeth. Typically, the attachments are fabricated of stainless steel, porcelain (ceramic), plastic, or combinations of these materials. The attachments serve as a standardized "handle" by which the tooth may be engaged by a force.

Each attachment in a system (generally referred to as a "bracket") possesses a rectangular slot that receives the arch-wire component. Typically, all the attachments of a particular system will have the same rectangular slot dimensions of about 0.018×0.025 inches, 0.020×0.025 inches or 0.022× 0.025 inches. Some operators prefer to use a combination of various size slots. The slot shape is rectangular to accommodate a wire with a rectangular or square cross section, which permits application of forces and hence control of tooth position in three dimensions.

Typically, arch-wires are made of metal alloys capable of varying degrees of elastic deflections depending on their size, cross-sectional shape, and composition. The elastic deflections in the arch-wire generate forces on the brackets, which in turn translate the forces to the teeth, thereby causing the teeth to move to a desired position.

The human teeth are arranged spatially in the upper or lower jaw (the maxillary or mandibular dental arches respectively) in the shape of an arch with their long axes generally perpendicular to the plane of the arch. The precise shape of the arch varies among individuals from more U-shaped arches to V-shaped arches to parabolic arch forms. The precise shape of any particular arch can vary substantially.

Given that the teeth are naturally arranged in this relatively flat-plane arch-form, it is commonly recognized as an objective of orthodontic therapy that this plane should be made relatively flat and that the teeth should be aligned precisely to form an arch-form shape that is similar (but improved) to the pre-existing condition of the dentition. To serve this objective, the "straight-wire", "pre-adjusted", or "pre-programmed" concept of appliance design was derived as a means of executing orthodontic therapy with greater ease, efficiency, and quality. The basic concept of "straight-wire" is that, if the objective of orthodontic therapy is to position teeth in a flat plane, then the force generated by elastic deformations in a flat, straight wire shaped in the form of an arch is an ideal mechanism for producing those results. In theory, the attachments are rigidly fixed to teeth at a precise "pre-adjusted" or "pre-programmed" position on the mid-facial or lingual aspect of a tooth at their respective mal-aligned state. A straight (flat) arch-shaped wire is then deflected to engage the mal-aligned attachments slots. The force generated by the elastic deformation of the wire then "pulls" the teeth along with it as it moves back towards its original shape. The attachment position on each tooth then determines the ultimate and final relative position of each tooth relative to the other teeth upon achievement of the "straight-wire" condition (the theoretical end-point).

Traditionally, the vast majority of orthodontic therapy has been performed with attachment slots placed primarily on the facial aspect of the teeth. It can be readily deduced via casual observation of an arch of teeth that the mid-facial aspects of an arch of teeth tend to align in a straight, flat arch form. However, it is also readily observed upon closer inspection that these mid-facial surfaces do not exactly line up in a straight line with their long axes residing at identical orientations. In fact, one can readily observed consistent deviations in the spatial relations of an arch of tooth crowns and roots. Each tooth type tends to deviate in a specific consistent "average" way relative to the horizontal plane. As such, early pioneers of appliance design theorized that compensations in bracket slot orientation relative to the bracket base could automatically compensate for these differences.

They also realized that the anatomy among types of teeth (upper right central incisor, versus, for instance, an upper right canine, etc.) varies substantially. But because this anatomy is consistent among different individuals for each tooth type, each tooth type, therefore, could receive its own uniquely shaped "average" bracket slot and base orientation. This pre-defined shape can theoretically be used on a particular tooth type for any particular individual. Thus, while the general shape of a bracket system might be very similar, for each particular tooth type the corresponding bracket is designed with specific compensations in base shape, base size, general shape, slot angulation, base thickness, etc. to accommodate differences in tooth type anatomy and tooth type spatial relations relative to the horizontal plane.

The intention of these design specifications was to create a universally applicable appliance that will, if brackets positions are accurately coordinated, create an ideal alignment of teeth if a straight wire is deflected into each slot and if the wire is subsequently permitted to express its original straight shape. By doing so, the operator would possess a pre-programmed mechanical system. Having realized a truly pre-programmed system, theoretically, the operator could eliminate the need for manual manipulation of the system (via the placement of compensating bends in the arch-wire component) and thus produce a highly predictable and efficient outcome.

However, as mentioned, the efficient utilization of a so-called straight-wire appliance depends largely on the orthodontist's ability to coordinate the position of the brackets on mal-aligned teeth so that the forces imposed by deflections of the resilient, straight, arch-wire will result in perfect three-dimensional alignment of the teeth. If the brackets are not properly positioned, then the degree of mal-positioning will be reflected as a proportional degree of mal-positioning of the teeth. Correcting these mal-positions would then require the operator to manually manipulate the shape of the arch-wire component via the placement of compensating arch-wire bends. This is recognized as a comparatively laborious, slow, unpredictable, and inefficient method.

Most orthodontists position the brackets on the patient's teeth using a "direct" method. "Direct" refers to the positioning of each bracket on each tooth directly, inside the patient's mouth. But when working directly inside the mouth it is very difficult to visualize precise bracket positioning and extremely cumbersome to utilize measuring instruments for determining vertical position. Because accurate positioning is so difficult, getting the bracket "close enough" is widely regarded as an acceptable compromise. Because precise positioning of an entire arch of brackets is the exception rather than the norm, the result is a huge compromise in treatment quality and efficiency.

To improve the accuracy of bracket positioning in a typical private practice setting, "indirect" positioning methods have been developed. Rather than positioning brackets directly inside the patient's mouth, the brackets are positioned on a three-dimensional model of the patient's teeth, outside the patient's mouth. In this way, improved visualization and the utilization of measuring devices are permitted, so accurate positioning becomes much more simple and attainable. Once the brackets are positioned on the model and rigidly attached, a "transfer tray" is fabricated and utilized to transfer the brackets from the model to the patient's mouth. The tray preserves the brackets position during the transfer. There are a number of known variations of indirect methods, including those described in U.S. Pat. No. 5,971,754 to Sondhi et al. and U.S. Pat. No. 4,952,142 to Nicholson, which are hereby incorporated herein by reference.

There are drawbacks to conventional bracket systems, regardless of the attachment method used. Typical brackets (both facial and lingual types) are composed of two basic structures. The first, a broad, flat base. Second, is a structure (s) protruding perpendicular to the base that forms the "open face" rectangular slot and the "tie-wings" that are used to anchor a disposable ligature that, in turn, maintains engagement of the wire component in the slot.

Generally, with a facial or lingual bracket system, all anterior and premolar brackets are designed with an open-face slot that allows the arch-wire component to be inserted into the slot along a facio-lingual vector. This bracket design requires the presence of tie-wings to engage and maintain engagement of the wire component. Because of the necessity of tie-wings, these brackets must possess a certain degree of structural profile height and shape irregularity that facilitates overall effectiveness and simple operation of the ligature/tie-wing ligation system by the operator.

Generally, with a facial or lingual bracket system, it is also common to use a tube attachment on molar teeth, rather than an open-face-slot bracket design. The tube type of attachment receives the arch-wire component via threading of the wire through the mesial or distal ends of the tube. This type of attachment has the benefit of not requiring the protruding, bulky, irregularly shaped tie-wings that are required of an open-face design. However, their applications are limited to the posterior teeth due to the necessity of threading the wire through the mesial or distal ends. It would be an impractical endeavor to attempt threading an arch-shaped wire through an entire dental arch starting from the most distal molar. Not only would the wire initial need to extend into the patients throat but the lack of a continuously consistent degree of curvature of the wire segment would preclude insertion of a wire of significant stiffness. In addition, the closed-face tube attachment precludes the placement of significant arch-wire bends, therefore, it is only practical if the attachment system is positioned with high precision and coordination.

As such, conventional bracket systems are designed to accommodate one bracket per tooth on either the facial or lingual side, but, as a practical matter, not both. They use open-face slots on anterior and most premolar teeth with tube attachments on the molar teeth. Note that many tube attachments designed for molars are also designed with a removable facial wall that allows the tube to be converted into an open-face bracket. Such designs also require the presence of tie-wings to hold the wire in place once the tube is converted to an open-face bracket.

The relatively large flat base characteristic of most conventional brackets serves several purposes. First, the relatively flat base is intended to rest against each tooth parallel to a tangent plane at the center of its mid-facial surface. This allows the operator the opportunity to use the surface of the tooth as a means of reference for establishing the properly coordinated position of each bracket—the operator simply must fully seat the bracket base against the tooth at its mid-facial surface. Doing so orients the slot at its recommended three-dimensional pre-programmed (pre-coordinated) position. Second, the base serves as the bonding interface for rigid attachment to the tooth. As such, the "tooth-side" of the base generally possesses mechanical retentive features (such as a mesh pad, particle micro-etched surface, laser-etched surface, etc.) that facilitates durable bonding to the tooth by facilitating mechanical interlocking between an adhesive and the bracket via penetration of the adhesive into the retentive features. Some brackets, depending on their material composition, may also possess a base that bonds chemically to an adhesive. The base is relatively flat and large to provide a sufficient surface area for creating a durable bond to the tooth.

But a base of any substantial length compromises the ability to custom-coordinate positioning of a bracket in particular ways. For example, if the operator desires to place the slot at an alternative facio-lingual angle, the base interferes and creates an undesirable lever arm that necessitates displacement of the slot in an unfavorable way, a greater distance from the tooth surface. As such, to achieve coordination of the remaining bracket slots would require positioning them with an equal degree of offset away from the tooth surface. Moreover, with the bracket now positioned farther from the tooth, that is, creating a higher, more protruding profile, the bracket is more prominent and protruding so as to physically annoy a patient. And even when the bracket can be positioned with the base flat against the tooth, the width of conventional brackets alone makes them comparably protrusive, when most patients would prefer them to be minimally protrusive.

In addition, because lingual side tooth anatomy is more highly variable among individual tooth types compared with facial side anatomy, using a "base-dependent" positioning system to achieve a "straight-wire" result is even less efficient than the traditional facial bracket system. That is, a "fixed bracket shape with a base" designed for the lingual tooth surface is remarkably less efficient at achieving coordination of slot positions such that a straight wire could then deflect the teeth to the desired positions. Because of this inefficiency, greater effort and greater unpredictability are realized by the operator who attempts to bend arch-wire to compensate for poorly coordinated lingual bracket slots.

If an operator desires the efficiency of a straight wire mechanical system to be used on the lingual side of teeth, this requires the ability to customize slot position for each patient. While this can theoretically be accomplished using a traditional bracket with a base and protruding tie-wings, the degree of protrusion and irregularity of shape (roughness) creates substantial discomfort for the patient. For this reason and others, lingual bracket systems have seen only very limited applications in orthodontics.

In addition, the desirability of adjustability has lead to the predominant use of open-faced slots. In fact, open-faced slots are a practical necessity because of the obvious problem that a wire possessing compensating bends of significant size cannot be threaded through tubes of small cross-section and the obvious problems with insertion of full-length arch-wires through a closed-face bracket system. But with open-faced slots, the arch-wires must be secured, which is conventionally done by using ligature tie-wings. And the tie-wings create a relatively bulky, high profile bracket system and generally result in a highly irregular surface against which lips, cheeks, and tongue will rub and create discomfort.

Because of the cost associated with the vast inventory of brackets required, most operators use a manufacturer-specified shape (not a shape customized to the unique dental anatomy of the patient) for each tooth. Existing brackets do not allow for minimizing the profile and protuberances, which would create a far more comfortable lingual bracket system. The necessity of having tie-wings to engage ligature ties for the purpose of holding the wire engaged in the slot means that uncomfortably large, irregular protuberances are unavoidable.

Accordingly, there is a need for an orthodontic bracket that has a lower profile and smoother contour, can be positioned on the lingual side of the teeth without compromising patient comfort, is less visibly noticeable, and can be positioned with great precision and flexibility. It is to the provision of such an orthodontic bracket and attachment method that the present invention is primarily directed.

SUMMARY OF THE INVENTION

One aspect of the present invention includes an orthodontic bracket for use with a wire to reposition a tooth. Generally described, the bracket includes a body with an opening that extends the length of the body for receiving the wire in it. The body of the bracket does not have a base with a significant surface area to facilitate use of a direct method of positioning and bonding the bracket to the tooth and thus fixing the position of the opening. Rather, because the bracket does not possess a base, the bracket, as a practical matter, incorporates an indirect method of precise positioning relative to a model tooth's anatomic features without any part of the bracket creating a significant lever arm that would cause the bracket to have a higher effective profile. In exemplary embodiments of the bracket, the body has a gingival sidewall, an occlusal sidewall, and a lingual sidewall that together form a slotted opening with the open side facing the tooth. The bracket has a very a low profile with a width that is equal to the depth of the opening plus the thickness of the lingual sidewall.

The bracket can be positioned offset from the model tooth or adjacent to it. When the bracket is offset from the model tooth, then it is suspended by, for example, a positioning instrument that also registers the relevant anatomic features, preferably with no part of the bracket contacting the model tooth. And when the bracket is adjacent to the model tooth, then the gingival sidewall, the occlusal sidewall, or both may contact the model tooth at some point along its length.

Preferably, the opening is rectangular and the bracket can be positioned adjacent to or offset from a generally vertical or non-vertical surface of the model tooth with the rectangular opening precisely positioned spatially at a desired position. In some embodiments, the occlusal sidewall length is greater than the gingival sidewall length, such that the open tooth side of the opening is angled from vertical.

In addition, the bracket may include one or more retention flanges extending from the body for enhanced bonding strength. In these embodiments, the retention flanges do not add substantially to the bracket's profile width, and thus, it retains its low profile width with the profile width being effectively equal to the opening depth plus the lingual sidewall thickness. Preferably, the opening is rectangular and the flanges are angled relative to the rectangular opening and tooth surface such that the flanges do not interfere with its spatial orientation by acting as a lever arm against the tooth. In this way, the bracket can be positioned adjacent to or offset from a vertical or a non-vertical surface of the tooth with the rectangular opening still level. In some embodiments, the flanges curve away from the tooth as they extend away from the opening. For example, in some embodiments for use on back teeth, one of the flanges extends from a gingival sidewall of the body and is curved back as the flange extends away from the opening. And another of the flanges extends from an occlusal sidewall of the body and is curved back as the flange extends away from the opening. But in other embodiments for use on the lingual surface of front teeth, the other flange that extends from an occlusal sidewall of the body is curved forward as the flange extends away from the opening.

In alternative embodiments, the bracket has notches or slits that promote enhanced bonding strength, a laterally curved body and opening, two or more of the openings, and/or a tubular opening.

Another aspect of the present invention includes an orthodontic attachment for use with a wire to reposition a tooth. Generally described, the attachment includes a mass of adhesive bonded to the tooth and an orthodontic bracket embedded in the adhesive mass. Preferably, the adhesive mass encapsulates the bracket except for the opening. The adhesive mass and the bracket can be attached to a lingual or facial surface of the tooth. The attachment may include a bracket of the type described herein or another.

Yet another aspect of the present invention includes an orthodontic appliance for repositioning a plurality of teeth. Generally described, the appliance includes a series of orthodontic attachments attached to the teeth and receiving a wire. Preferably, some of the attachments are attached to lingual surfaces of the front teeth. For the back teeth, the appliance attachments may be attached to the lingual or facial tooth surfaces. The appliance may include attachments made using a bracket of the type described herein or another.

Still another aspect of the present invention includes a clip for holding an orthodontic bracket having an opening. Generally described, the clip has a finger that is received in the bracket opening and a handle portion for grasping. The finger has a length that is equal to or greater than the length of the bracket opening so that the finger extends all the way through the opening to prevent the adhesive from intruding into and blocking the opening. Preferably, the finger is configured so that it fits snugly in the opening. In this way, the clip can be held by the handle portion and the clip will support the bracket. For example, the finger may have a cross sectional shape and a lateral curvature that conform to a cross sectional shape and a lateral curvature of the bracket opening. In addition, the handle portion is preferably keyed for use with a keyed positioning tool, so that the clip can be consistently aligned when grasping it with the positioning tool.

And another aspect of the present invention includes an orthodontic kit comprising a plurality of orthodontic brackets and holding clips. Preferably, the bracket has a body and an opening that are configured for positioning the bracket offset from or adjacent to a tooth in a low profile arrangement. And the clip has a finger for insertion into the opening to hold the bracket and block adhesive from intruding into the opening. The bracket and clip may be of the types described herein or others.

Having described the brackets, attachments, appliances, and clips, another aspect of the present invention providing methods of using of the brackets and the clips to form the attachments and appliances will now be described. Generally described, a first exemplary method includes the steps of creating a model of the teeth and providing orthodontic brackets with openings for the wire, with the brackets preferably of the type described herein. Next, the method includes the steps of positioning the brackets relative to the model teeth, occluding the bracket openings, bonding the brackets to the model teeth with an adhesive, fabricating a transfer tray by applying an impression material to the model teeth and the brackets, removing the tray containing the impression material and the brackets from the model teeth with the brackets held in position by the impression material, positioning the tray with the brackets on the teeth, bonding the brackets to the teeth with an adhesive, removing the tray from the brackets and teeth, and unoccluding the bracket openings by removing the clips. Upon the completion of the method, the adhesive is bonded to the teeth, preferably using the same adhesive, and the brackets are embedded in the adhesive with the openings unobstructed.

Preferably, the step of positioning the brackets includes, for each of the brackets, providing a clip of the type described herein for holding the bracket and moving the bracket/clip unit until the bracket is positioned. In addition, the step of occluding the bracket opening may include inserting a finger of the clip into the bracket opening, and the step of unoccluding the bracket opening may include removing the finger from the bracket opening. Moreover, the step of positioning the brackets may involve grasping the handle portion of the clip by a positioning tool or machine.

The step of positioning the brackets further includes, for each of the brackets, positioning the bracket offset from or adjacent to the corresponding tooth, as is appropriate for that particular tooth. This step may also include positioning some of the brackets at the lingual surfaces of the front teeth and positioning some of the brackets at the facial surfaces of the back in an overlapping arrangement.

In addition, preferably, the steps of bonding the brackets to the model teeth and forming the transfer tray includes a means of creating a smooth adhesive mass that encapsulates the brackets except for the slot openings. For example, adhesive can be added to the model and bracket to create the adhesive mass and then the transfer tray can be formed around this adhesive mass using preferred impressions materials. Or, for example, instead of forming the entire adhesive mass by adding adhesive to the model, a void can be created in the impression material by adding a prior shell that surrounds the bracket and clip unit in a preferred way. The adhesive mass then is formed in a subsequent step immediately prior to inserting the transfer tray inside the patients mouth where the adhesive is added to the void to over-fill it slightly such that the adhesive both forms the completed, smooth surface attachment delimited by the shell and simultaneously bonds the bracket to the tooth.

Generally described, a second exemplary method includes the steps of positioning the brackets suspended in free space and offset from the teeth. This step is preferably done by generating a 3D virtual model of the teeth, digitally manipulating virtual brackets with six degrees of freedom and with no part of the virtual brackets acting as a lever arm against the virtual teeth, and digitally positioning the virtual brackets suspended in free space and offset from or contacting the virtual teeth. This is preferably done using proprietary software. Alternatively, this step can be done by using a bracket-positioning machine or by another means such as by robotic arm.

Next, the method includes fabricating a transfer tray with voids and attachment elements, with the voids for receiving the brackets and the attachment elements for registering the specified positions of the brackets. This is preferably done by using the proprietary software to digitally generate a virtual transfer tray for holding the virtual brackets in the specified positions offset from the virtual teeth. The virtual transfer tray has virtual voids and attachment elements corresponding to the physical ones. Then the transfer tray is fabricated as a replica of the virtual transfer tray. Preferably, the fabrication is done by using a rapid prototyping system.

In the next step, the transfer tray is prepared for use. This includes occluding the bracket openings and inserting the brackets into the voids in the positions registered by the attachment elements. Preferably, clips are provided with fingers that the brackets slide onto, the transfer tray is provided with a slot extending from the void through an outer surface of the transfer tray, and the clips fit into the slots, thereby holding the brackets in the proper positions within the voids. Then the voids are filled with adhesive masses to encapsulate the brackets, except for the bracket openings, which are occluded by the clip fingers.

Now the transfer tray is ready for use. The transfer tray is placed on the physical teeth and the adhesive masses are cured to bond the encapsulated brackets in position offset from the physical teeth. Next, the transfer tray is removed from the teeth, leaving the adhesive masses attached to the teeth, the brackets encapsulated within the adhesive masses, and the clip fingers in the bracket openings. This is because the fingers break off of the clips when the transfer tray is removed. Then the clip fingers are removed from the bracket openings, and the orthodontic attachments are complete. Finally, a wire is routed through the bracket openings to form the completed orthodontic appliance.

Accordingly, the present invention provides orthodontic brackets that have a minimal size profile to enhance patient comfort and that can be placed on the lingual side of teeth to minimize visibility and at the same time are extremely flexible in the positions in which they can be oriented to form orthodontic attachments and appliances. Because of this flexibility, the brackets and methods of attachment can be used to reposition teeth much more quickly and with much less patient discomfort while minimizing visibility of the appliances.

The specific techniques and structures employed by the invention to improve over the drawbacks of the prior devices and accomplish the advantages described herein will become apparent from the following detailed description of the exemplary embodiments of the invention and the appended drawings and claims.

BRIEF DESCRIPTION OF THE DRAWINGS

FIG. 2 is a perspective view of an orthodontic bracket according to a first exemplary embodiment of the present invention, showing an opening for an arch-wire and wings for bonding strength.

FIG. 3 is a side view of an orthodontic attachment including the orthodontic bracket of FIG. 2 attached to the lingual surface of an incisor tooth.

FIG. 4 is a side view of an orthodontic attachment including the orthodontic bracket of FIG. 2 attached to the lingual surface of a canine tooth.

FIG. 5A is a perspective view of a first alternative embodiment of the orthodontic bracket of FIG. 2, showing notched edges in the flanges.

FIG. 5B is a perspective view of a second alternative embodiment of the orthodontic bracket of FIG. 2, showing the bracket body and opening being laterally curved.

FIG. 6 is a side view of an orthodontic bracket according to a second exemplary embodiment, showing flanges swept back on both sides.

FIG. 7 is a side view of an orthodontic attachment including the orthodontic bracket of FIG. 6 attached to a generally vertical surface of a molar tooth.

FIG. 8 is a side view of an orthodontic attachment including the orthodontic bracket of FIG. 6 attached to a sloped surface of a molar tooth.

FIG. 9 is a side view of a first alternative embodiment of the orthodontic bracket of FIG. 6, showing the bracket body having two arch-wire openings.

FIG. 10 is a side view of an orthodontic attachment including the orthodontic bracket of FIG. 9 attached to a surface of a molar tooth.

DETAILED DESCRIPTION OF EXEMPLARY EMBODIMENTS

Figure 1A:
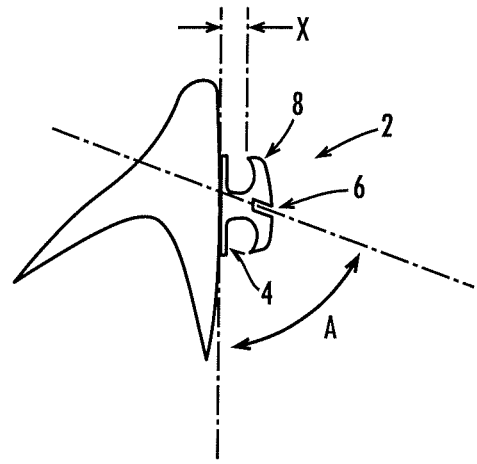
FIG. 1A is a side view of a prior art orthodontic bracket.
Figure 1B:
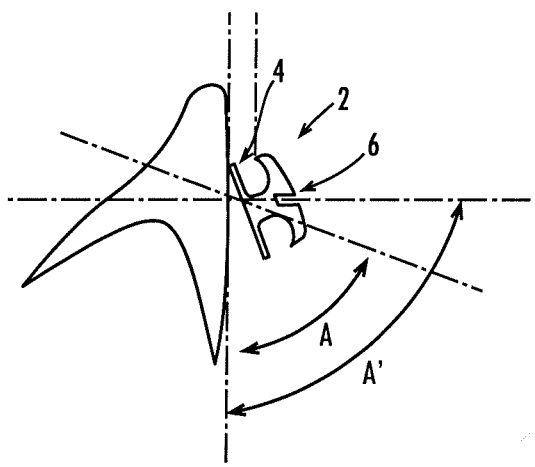
FIG. 1B is a side view of the prior art orthodontic bracket of FIG. 1, showing the limitation on rotational positioning of the bracket.
Figure 1C:
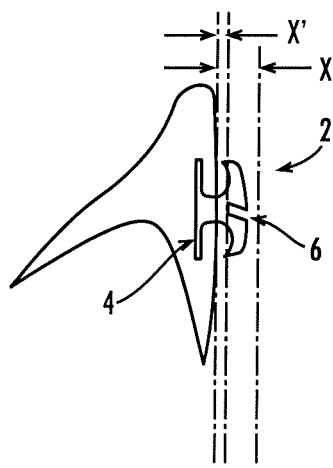
FIG. 1C is a side view of the prior art orthodontic bracket of FIG. 1, showing the limitation on in/out positioning of the bracket.

Referring to the drawings, FIGS. 1A-C illustrate a conventional prior art orthodontic bracket 2. The bracket has a flat base 4 with a large surface area for bonding to a tooth, a rectangular slot 6 for a rectangular wire, and tie wings 8 for tying down the wire in the slot. Once the base 4 is positioned against the tooth, the orientation and position of the slot 6 are fixed and cannot be easily customized. In particular, the bracket 2 cannot be easily rotated to adjust the angle A of the slot 6 relative to the tooth, for example, to an increased angle A', without the base 4 acting as a lever arm that increases the in/out position of the slot relative to the tooth (see FIG. 1B). And the bracket 2 cannot be moved horizontally to adjust the in/out position X of the slot 6 relative to the tooth, for example, to a decreased in/out position X', because of interference with the tooth (see FIG. 1C). As such, the bracket slot 6 is offset a good distance from the tooth surface, giving the bracket a relatively high profile and making it somewhat uncomfortable for the patient. And because the bracket depends upon the regularity of the facial tooth surface for its proper orientation, the bracket can only be used practically on the facial surfaces of front teeth.

Orthodontic Brackets

Referring now FIG. 2-4, there is illustrated an orthodontic bracket 10 according to a first exemplary embodiment of the present invention. The bracket 10 is positioned relative to a tooth 12 and used to form an orthodontic attachment 14 that receives an arch-wire (not shown) to reposition the tooth 12. In a typical commercial embodiment, the bracket 10 is used with arch-wire that is of a maximum cross-sectional dimension of 0.014×0.022 inch rectangular metal wire. As used herein, the terms "arch-wire" and "wire" mean any elongated force-imparting member that may be used with orthodontic attachments for repositioning teeth. Accordingly, the wire may be circular, have another shape, be larger or smaller, and/or may be made of plastic or another material. In addition, a typical commercial embodiment of the bracket 10 is made of metal by forging, casting, or other techniques. It will be understood, however, that other fabrication techniques and materials may be used, such as plastics, ceramics, carbon fiber materials, and composites. Furthermore, the bracket 10 is primarily, though not exclusively, for use on the lingual surface of incisors and other front teeth, while other-described embodiments are primarily for use on molars and other back teeth.

The bracket 10 has a body 16 with an opening 18 for receiving the wire in it. The opening 18 is coextensive with the body 16, that is, it extends the length of the body so that the opening is open at both ends of the body. Preferably, the body 16 has a gingival sidewall 20, an occlusal sidewall 22, and a lingual sidewall 24 that together form the opening 18 as a rectangular slot with its open side facing the tooth 12. In typical commercial embodiments, the bracket 10 is provided in lengths of 1.5 mm and 3 mm, for use on different-sized teeth, and the opening 18 is rectangular with a cross section dimension of 0.016×0.024 inch. It will be understood, however, that other sizes and shapes of bodies and openings can be provided. For example, the opening may be of a cross-sectional shape that is circular, semi-circular, ovoid, or other, and/or of a closed tube design. It is understood that the rectangular shape reflects an embodiment currently preferred by most practitioners and that its purpose, to engage a force in three dimensions, may be realized by alternative shapes.

The body 16 of the bracket 10 does not have a flat (or other shaped) base with a broad surface area for bonding directly to the tooth and fixing the position of the opening, as do conventional brackets. Instead, the bracket 10 can be positioned in free space with the opening 18 at a customized, pre-selected angle relative to the tooth surface 12, and can be oriented with six degrees of freedom, without any part of the body 16 creating a lever arm against the tooth surface. In this way, the bracket 10 can be oriented in a wide range of positions while maintaining a low profile and low visibility.

In addition, the bracket body 16 preferably includes retention flanges 26' and 26b" (collectively, the "flanges 26") extending from it. The flanges 26 serve to distribute forces imposed upon the bracket over a larger area of the adhesive component such that stresses will be less concentrated in any particular area of the adhesive thus improving the overall integrity of the attachment structure. These flanges 26 extend away from the tooth surface so as to avoid creating a lever arm against the tooth surface and increasing the in/out position of the opening 18. In this configuration, the bracket 10 retains its low profile, with its width being equal to the depth of the opening 18 plus the thickness of the lingual sidewall 24 plus the horizontal extension of the flanges 26.

Preferably, the flanges 26 are angled relative to the rectangular opening 18 so that the bracket 10 can be positioned adjacent to or offset from a vertical or a non-vertical surface of the tooth 12 with the rectangular opening still level. More particularly, in a typical commercial embodiment, the flanges 26 curve away from the tooth 12 as they extend away from the opening 18, so that if the flanges were extended across the opening they would form a continuous convex surface. For example, because the bracket 10 is primarily for use on the lingual surface of incisors and other front teeth, the gingival flange 26" extends from the gingival sidewall 20 of the body and is curved back as it extends away from the opening 18. And the occlusal flange 26' extends from the occlusal sidewall 22 of the body and is curved forward as the flange extends away from the opening 18.

In addition, the occlusal sidewall length is preferably greater than the gingival sidewall length, so that the open side of the opening 18 is angled from vertical. In this preferred configuration, the bracket 10 has an extremely low profile that is not compromised by adjusting its position to get the opening 18 into a desired position.

Referring particularly to FIGS. 3 and 4, the bracket 10 can be used to form the low profile orthodontic attachment 14 on different angled surfaces of teeth 12. When forming the attachment 14, the bracket 10 can be positioned offset from or adjacent to a vertical or a non-vertical surface of the tooth 12, as may be needed to position the bracket so that at the conclusion of the treatment the rectangular opening 18 is level. When the bracket 10 is offset from the tooth 12, then the bracket is suspended with no part of the bracket contacting the tooth. And when the bracket 10 is adjacent to the tooth 12, then the gingival sidewall 20, the occlusal sidewall 22, or both contact or almost contact the tooth. For example, when the bracket 10 is used to form an attachment 14 on the lingual surface of the incisor tooth 12 of FIG. 3, the gingival sidewall 20 is slightly offset from or adjacent to the tooth and the occlusal sidewall 22 is more offset from the tooth. But when the bracket 10 is used to form an attachment 14 on the more vertically sloped lingual surface of the canine tooth 12 of FIG. 4, the occlusal sidewall 20 is slightly offset from or adjacent to the tooth and the gingival sidewall 22 is more offset from the tooth. And in both cases, the rectangular opening 18 is oriented level, that is, squared to horizontal and vertical, and positioned spatially in an ideal way for coordination with the adjacent brackets so that their openings (and thus the arch-wire that is later inserted into the openings) form a continuous and smooth arch at the conclusion of the orthodontic treatment. Furthermore, this flexibility permits using the same type of bracket 10 on other-sloped tooth surfaces, including at higher or lower positions of the same tooth and on different teeth. Details of the preferred methods of using the bracket 10 to form the attachment are provided below.

Figure 5C:
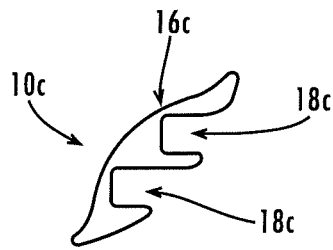
FIG. 5C is a side view of a third alternative embodiment of the orthodontic bracket of FIG. 2, showing the bracket body having two arch-wire openings.

Referring to FIGS. 5A-5I, there are shown several of the possible alternative embodiments of the bracket 10. FIG. 5A shows a bracket 10a according to a first alternative embodiment, in which the flanges 26a' and 26a" of the body 16a have notches 28a. The notches 28a reduce the tendency of fracture planes forming in the bonding material, thereby providing increased bonding strength. Towards this end, the notches can be deeper or shallower, greater or lesser in number, and/or made in a curved, triangular, squared, or other shape, as may be desired.

FIG. 5B shows a bracket 10b according to a second alternative embodiment, in which the bracket body 16b and opening 18b are laterally curved. In this configuration, the curved opening 18b more closely conforms to the curvature of the arch of the teeth, which defines the curvature of the arch-wire. Thus, when the wire is installed in the opening 18b, it can curve slightly so that it does not need such a sharp bend upon exiting the opening at its ends. And the curved body can be rotated slightly at the mesial or distal end (about a vertical axis) to orient the opening while maintaining a low profile.

FIG. 5C shows a bracket 10c according to a third alternative embodiment, in which the bracket body 16c has two openings 18c. In this configuration, the bracket 10c can be used to form attachments that make up a sectionalized orthodontic appliance that accommodates the insertion of multiple wire segments, as will be described in more detail below.

Figure 5D:
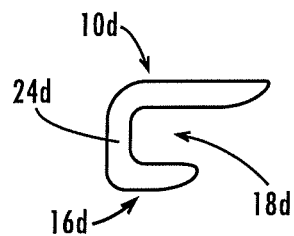
FIG. 5D is a side view of a fourth alternative embodiment of the orthodontic bracket of FIG. 2, showing the bracket without flanges.

FIG. 5D shows a bracket 10d according to a fourth alternative embodiment, in which the bracket body 16d has no flanges. In this configuration, the bracket 10d has a low profile, with a width that is equal to the depth of the opening 18d plus the thickness of the distal sidewall 24d.

Figure 5E:
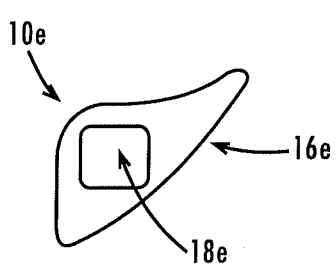
FIG. 5E is a side view of a fifth alternative embodiment of the orthodontic bracket of FIG. 2, showing the bracket having a tubular opening.

FIG. 5E shows a bracket 10e according to a fifth alternative embodiment, in which the bracket opening 18e is tubular and the bracket body 16e has four sidewalls defining the tubular opening. In this configuration, there is more bracket body surface area for bonding and a grasping clip can be more easily removed from the opening because the adhesive does not contact it. But the bracket 10e may not be quite as low in profile and may be more costly to manufacture. Accordingly, instead of the tubular opening 18e being completely closed, the fourth (tooth-side) sidewall may be thin and extend across the opening from the occlusal side but stop short of the gingival side (leaving a gap), thereby eliminating the width that would otherwise be added by the fourth sidewall.

Figure 5F:
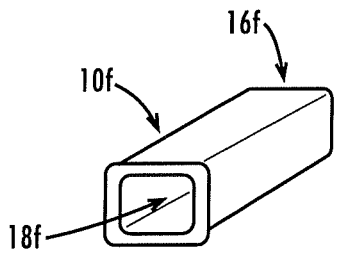
FIG. 5F is a perspective view of a sixth alternative embodiment of the orthodontic bracket of FIG. 2, showing the bracket having a tubular opening and generally uniformly thick sidewalls.

FIG. 5F shows a bracket 10f according to a sixth alternative embodiment, in which the bracket opening 18f is tubular and the bracket body 16f has four sidewalls of generally uniform thickness defining the tubular opening.

Figure 5G:
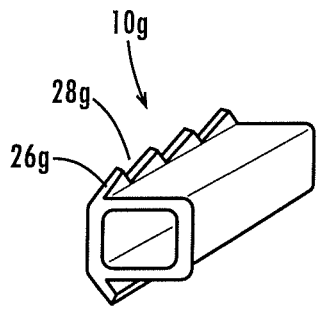
FIG. 5G is a perspective view of a seventh alternative embodiment of the orthodontic bracket of FIG. 5F, showing the bracket having retention flanges with notched edges.

FIG. 5G shows a bracket 10g according to a seventh alternative embodiment, in which the bracket has retention flanges 26g with notched edges 28g.

Figure 5H:
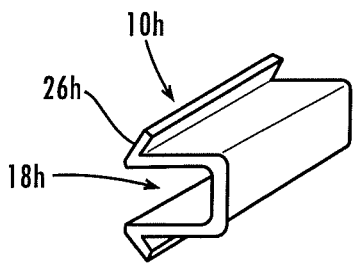
FIG. 5H is a perspective view of an eighth alternative embodiment of the orthodontic bracket of FIG. 2, showing the bracket having generally uniformly thick sidewalls and retention flanges.

FIG. 5H shows a bracket 10h according to an eighth alternative embodiment, in which the bracket opening 18h has an open side unnotched retention flanges 26h.

Figure 5I:
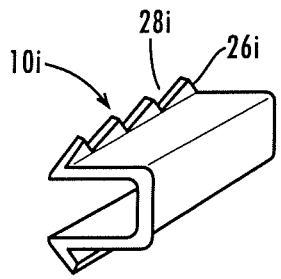
FIG. 5I is a perspective view of a ninth alternative embodiment of the orthodontic bracket of FIG. 5H, showing the bracket having notched edges in its retention flanges.

FIG. 5I shows a bracket 10i according to a ninth alternative embodiment, in which the bracket retention flanges 26i with notched edges 28i.

In another alternative embodiment, the bracket body has one or more inner flanges for assisting in holding the bracket on a grasping clip. In yet another alternative embodiment, the bracket body has a lingual sidewall and gripping arms extending from opposite ends of it that together define the opening, with the gripping arms configured for holding the bracket on a grasping clip. In still another alternative embodiment, the bracket body is generally L-shaped and rests on a grasping clip, with or without gripping arms. In another alternative embodiment, the bracket body is generally triangular-shaped with the opening in the long side. In yet other alternative embodiments, the bracket has two openings that are aligned but with a gap between them, that are vertically overlapping and laterally staggered, or that are stacked horizontally. And in still another alternative embodiment, the bracket opening is at the gingival, occlusal, or lingual side of the bracket body.

Referring to FIGS. 6-8, there is shown an orthodontic bracket 110 according to a second exemplary embodiment of the present invention. While the bracket 10 of the first exemplary embodiment is primarily for use on the lingual surface of incisors and other front teeth 12, the bracket 110 of the second exemplary embodiment is primarily, but not exclusively, for use on the facial or lingual surfaces of molars and other back teeth 112. Because these surfaces are generally much closer to vertical than the lingual surfaces of incisors where the brackets 10 are attached, the bracket 110 has an opening 118 and flanges 126 that are configured differently.

In particular, the opposing sidewalls that form the opening 118 have the same length, or about the same. And both the flanges 126 are swept back so that they curve back symmetrically as they extend away from the opening 118. In this configuration, the bracket 110 can be positioned in a wide range of low profile positions. For example, FIG. 7 shows an orthodontic attachment 114 with the bracket 110 positioned adjacent a generally vertical surface of a premolar tooth 112, and FIG. 8 shows that same bracket positioned adjacent to a sloped surface of a molar tooth. In both cases, the bracket 110 and resulting attachment 114 are low profile, with the rectangular opening 118 still level and at a preferred spatial orientation.

FIGS. 9 and 10 show a bracket 110a according to a first alternative to the second exemplary embodiment, in which the bracket body 116a has two openings 118a. In this configuration, the bracket 110a can be used to form attachments 114a that make up a sectionalized orthodontic appliance, as will be described in more detail below. It will be understood that the alternative features described above with respect to the first exemplary embodiment can be implemented as alternative embodiments to the second exemplary embodiment.

Orthodontic Attachments Made Using the Brackets

Referring back to FIG. 3, details of the orthodontic attachment 14 will now be provided. The attachment 14 includes a mass of adhesive 30 bonded to the tooth 12 and an orthodontic bracket 10 bonded within the adhesive mass. The adhesive 30 is preferably provided by a generally white-colored optically curable compound. By using an adhesive 30 with a color and translucency that resemble the color and translucency of teeth, the attachment 14 is less noticeable. Alternatively, the attachment 14 may be formed using other bonding agents.

The bracket 10 is selected for forming the attachment 14 on a lingual or facial surface of the tooth 12, as desired. The attachment 14 is preferably made using one of the brackets 10 or 110 described herein. This way, the bracket 10 can be positioned offset from or adjacent to the tooth 12 while maintaining the desired orientation of the opening 18, so that the profile and visibility of the resulting attachment is minimized. Other types of brackets can be used, but to lesser advantage.

Preferably, the adhesive mass 30 encapsulates the bracket 10, except for the opening 18. In this configuration, the attachment 14 has a nice, smooth, continuous outer surface where the tongue and/cheeks might rub against it. Alternatively, the bracket 10 can be embedded in the adhesive mass 30, but not encapsulated, so that a portion of the body 16 remains exposed. In this configuration, the width of the attachment 14 is minimized. In any case, when using a bracket 10 with a slotted opening 18, the adhesive mass 30 defines a fourth wall of the opening.

Orthodontic Appliance Made from a Series of the Attachments

Figures 11, 12:
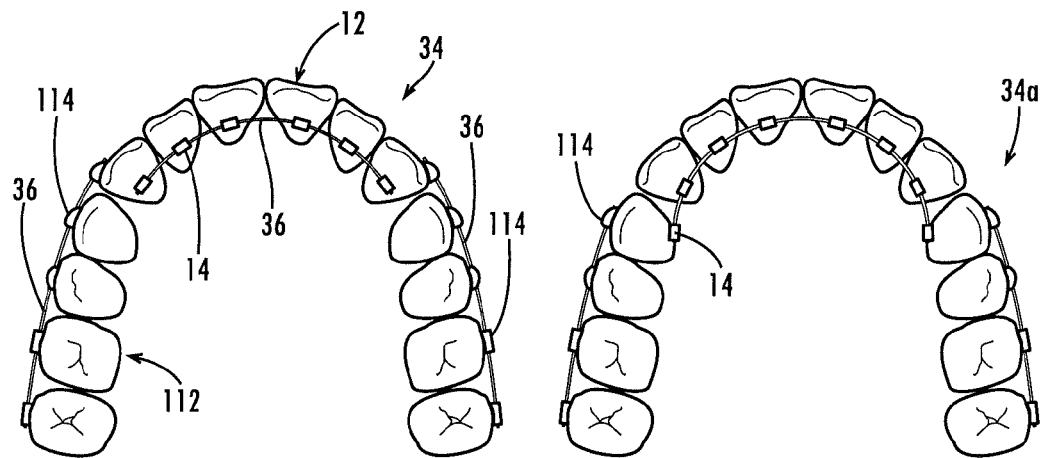
FIG. 11 is a plan view of an arch of teeth showing an orthodontic appliance including six of the attachments of FIG. 2 on lingual surfaces of front teeth and two sets of five of the attachments of FIG. 6 on facial surfaces of back teeth.
FIG. 12 is a plan view of an arch of teeth showing an orthodontic appliance including eight of the attachments of FIG. 2 on lingual surfaces of front teeth and two sets of four of the attachments of FIG. 6 on facial surfaces of back teeth.

Turning now to FIG. 11, there is shown an exemplary embodiment of an orthodontic appliance 34 made from a series of the attachments 14 and 114 mounted on an arch of teeth 12 and 112, with arch-wires 36 routed through the openings of the attachments and secured in placed by, for example, composite stoppers (not shown) at the wire ends and/or at some point between the teeth. The figure shows the teeth 12 and 112 after the appliance 34 has been used to reposition them to their proper positions. When the appliance 34 is initially installed, the attachments 14 and 114 are not so nicely aligned and the wire 36 is not so nicely and smoothly arched. Instead, the initially bent wire 36 imparts forces to the nonaligned attachments 14 and 114, which in turn pushes/pulls the teeth 12 and 112 towards the position in the figure.

In the embodiment shown, the appliance 34 includes six of the attachments 14 on lingual surfaces of six anterior teeth 12 and two sets of five of the attachments 114 on facial surfaces of posterior teeth 112. In this way, the appliance 34 is sectionalized into two back teeth sections that overlap with one front teeth section to simulate the effect of one continuous, straight wire. In this context, "overlapping" means that more than one of the appliance sections are present on a particular tooth, even if the sections each terminate shy of each other (so that a vertical line can not be drawn through them both). Preferably, the front teeth section overlaps with the back teeth sections, as shown, by virtue of at least one tooth (the canine in this example) possessing both facial and lingual attachments. Because the wire sections are disconnected, the absolute vertical position of each wire section can thus exist independently of the absolute vertical position of the other sections allowing more flexibility in the vertical position of these sections. In other words, bracket positions can be coordinated within each section independently of the other sections, thus, one section may exist at a higher or lower position in relation to the other sections. Also, because the spatial position of the attachments can be highly customized with precision (using a precision positioning instrument), the attachments may be positioned with the higher degree of accuracy required to create a straight-wire system out of disconnected multiple sections of wire.

The appliance 34 is preferably made using the attachments 14 or 114 described herein, so that the appliance has a low profile and is, therefore, not so noticeable. In this way, one or more of the attachments can be formed having their brackets positioned adjacent to their corresponding teeth, and one or more other of the attachments can be formed having their brackets positioned offset from their corresponding teeth, as may be needed to make appliance have a smooth arch-form to minimize the bending needed in the wire. Other types of attachments and brackets can be used, but to lesser advantage.

Figures 13, 14:
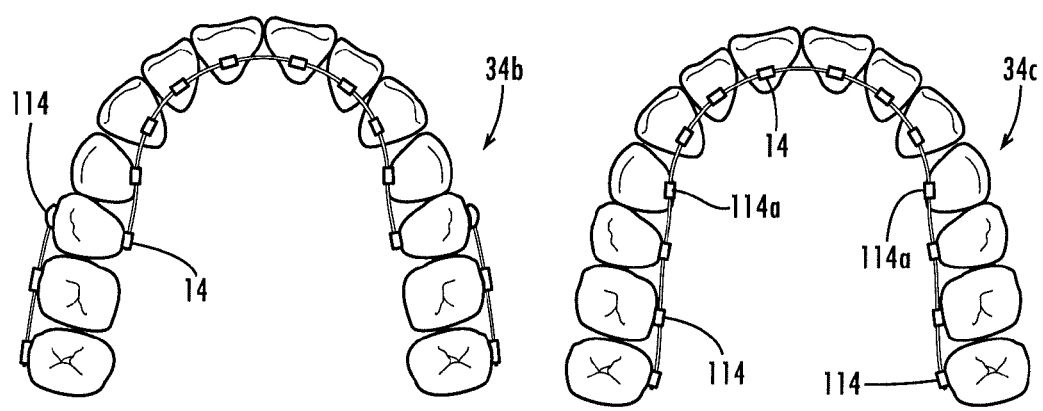
FIG. 13 is a plan view of an arch of teeth showing an orthodontic appliance including ten of the attachments of FIG. 2 on lingual surfaces of front teeth and two sets of three of the attachments of FIG. 6 on facial surfaces of back teeth.
FIG. 14 is a plan view of an arch of teeth showing an orthodontic appliance including the attachments of FIGS. 2 and 6 on lingual surfaces of front and back teeth and including the attachments of FIG. 5C or 9 on lingual surfaces of intermediate teeth.

FIG. 12 shows an alternative appliance 34*a* having three wire sections, the first being eight of the attachments 14 on lingual surfaces of front teeth 12 teeth and two sets of four of the attachments 114 on facial surfaces of back teeth 112. Similarly, FIG. 13 shows another alternative appliance 34*b* having five sections of wire, ten of the attachments 14 on lingual surfaces of front-most ten teeth 12, two sets of four attachments on the two premolar teeth with two single attachments placed on the lingual of first premolar teeth to serve as the anterior overlap point. Then two sets of three of the attachments 114 on facial surfaces of back teeth 112 including another overlap point on the second premolar that has both facial and lingual attachments. And FIG. 14 shows yet another alternative appliance 34*c* having various of the attachments all on lingual surfaces of the front and back teeth 12 and 112. In other alternative embodiments, the appliance can be formed using only single-opening attachments, only double-opening attachments, or any combination thereof, on only facial tooth surfaces, only lingual tooth surfaces, or any combination thereof. In other alternative embodiments, the appliance can be configured of as many or few overlapping sections as desired to simulate a continuous straight-wire system. Or the appliance may be configured with any combination of overlapping or non-overlapping sections, with either double- or single-tube attachments. Or, the appliance can be configured with one or multiple non-overlapping sections as deemed appropriate or possible for the achievement of particular objectives in any particular case.

Grasping Clip for Positioning the Brackets

Figure 15:
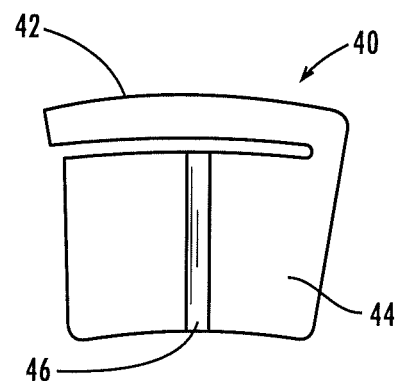
FIG. 15 is a plan view of a clip according to an exemplary embodiment of the present invention, for holding the bracket of FIG. 2.
Figure 16:
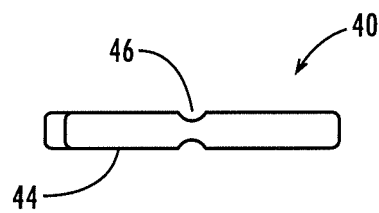
FIG. 16 is a side view of the clip of FIG. 15.
Figure 17:
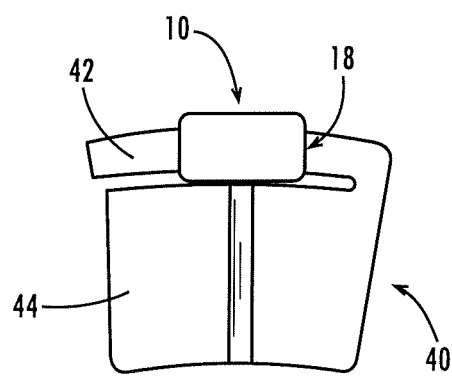
FIG. 17 is a plan view of the clip of FIG. 15 holding the bracket of FIG. 2, showing a clip finger received in the bracket opening.

Turning now to FIGS. 15-17, there is shown a grasping clip 40 according to an exemplary embodiment of the present invention. The clip 40 is used to hold the bracket 10 in position while it is being bonded to the tooth or model 12. The clip 40 is intended primarily for use with brackets of the type described herein, though it can be used with other orthodontic brackets to some advantage. The clip 40 is preferably a unitary piece of molded plastic, though it can be made of other materials using other fabrication techniques.

The clip 40 has a finger 42 that it is received in the bracket opening 18 and a handle portion 44 for grasping. The finger 42 has a length that is equal to or greater than the length of the bracket opening 18 so that the finger extends all the way through the opening to prevent the adhesive from intruding into and blocking the opening (meaning preventing or hindering the routing of the wire through the opening). In a typical commercial embodiment, the finger 42 has a length that is greater than 3 mm, so that it can be used with brackets up to that length. Preferably, the finger 42 is configured so that it fits snugly in the opening 18. For example, the finger 42 may have a cross sectional shape and a lateral curvature that conform to a cross sectional shape and a lateral curvature of the bracket opening. Thus, for use with the bracket 10*b* of FIG. 5B, the finger 42 would preferably be rectangular in cross section and laterally curved. In this way, the clip 40 can be held by the handle portion 44 and the clip will support the bracket 10 securely in position so that it doesn't move while it is being bonded to one of the teeth.

Figure 18:
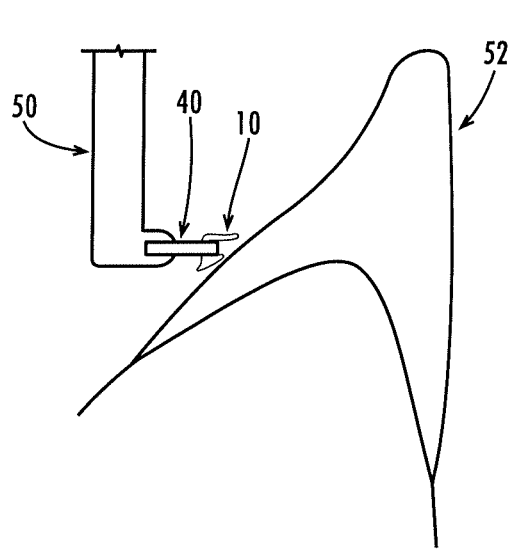
FIG. 18 is a side view of the bracket of FIG. 2 being positioned on model teeth, with the bracket held by the clip of FIG. 15, which is held by a positioning tool, according to a first exemplary method of the present invention.

The handle portion 44 is configured for being grasped by a person's hand and/or by a positioning tool 50 (see also FIG. 18). In this way, the bracket 10 can be held in place while the orthodontist bonds it to the corresponding tooth.

In addition, the handle 44 is preferably keyed for use with a keyed positioning tool, so that the clip 40 can be consistently aligned when grasping it with the positioning tool. For example, the handle 44 may have grooves 46 on both sides for receiving one or more ridges (not shown) on the positioning tool, or vice versa, so that the clip can be flipped either side up and still aligned and centered on the positioning tool.

In alternative embodiments, the clip has a finger with a detent for holding the bracket on it, the finger is keyed for use with matingly keyed bracket openings for centering or otherwise positioning the brackets on the clip, and/or the finger has a thin liner sleeve to which the adhesive bonds so that the sleeve tears away and stays in the bracket opening when the finger is removed. And in another alternative embodiment, the clip has two fingers for use with single- or double-opening brackets.

In another aspect of the present invention, there is provided an orthodontic kit that includes a plurality of the orthodontic brackets and grasping clips. The kit is not shown in the figures separately from its constituent parts, which are individually described and shown. Preferably, the brackets and clips are of any of the types described herein, though other brackets and/or clips can be provided.

Method of Attaching the Brackets to Teeth to Form the Appliance (Method One)

Turning now to FIGS. 18-23, there is shown a first exemplary method of attaching the brackets 10 to teeth 12 to form the attachments 14 and appliances 34. The method includes creating a model 52 of the teeth 12, which can be done by conventional techniques well known in the art, and providing orthodontic brackets 10 with openings for the wire. Preferably, brackets 10 of the type described herein are used, though others can be used to obtain some of the benefits of the method. Next, the brackets 10 are positioned relative to the model teeth 52, for example, with each bracket positioned and held by a grasping clip 40, which is moved into position and held there by a positioning tool or device 50, as shown in FIG. 18. The positioning tool or device 50 is preferably of the type disclosed in U.S. patent application Ser. No. 10/750,194, filed on Dec. 31, 2003, and entitled "Orthodontic Bracket Positioning Device And Method," which in its entirety is hereby incorporated herein by reference. Alternatively, the positioning tool or device may be of a conventional type known in the art, such as that disclosed by U.S. Pat. No. 4,812,118 to Creekmore, which in its entirety is hereby incorporated herein by reference.

Alternatively, the brackets can be physically placed on a physical model using a robotic system such as those commercially offered by Staubli Corporation (US HQ—Duncan, S.C.) or Nachi Robotic Systems, Inc. (US HQ—Novi, Mich.). Such robotic systems include a robotic arm controlled by programmed controllers. Robotic systems from both of these vendors were tested with actual dental models and brackets and proved to be of sufficiently high positional accuracy to perform the bracket placement. Using the robotic system to position the brackets requires more steps than using rapid prototyping (as described below), but to date the accuracy has been shown to be better for robots than for rapid prototyping. It will be understood that this robotic bracket-positioning step can be used with the transfer tray and clip described above for use in this method or with the modified transfer tray and clip described below in "method two."

The step of positioning the brackets 10 includes, for each of the brackets, positioning the bracket offset from or adjacent to the corresponding tooth 12, as is appropriate for that particular tooth, and preferably referencing relevant anatomical features of the particular tooth to determine its appropriate position and coordinating the position with other attachments of the relevant section. Also, this step may include positioning some of the brackets 10 at the lingual surfaces of the front teeth 12 and positioning some of the brackets at the facial surfaces of the back teeth 112 in an overlapping arrangement. In addition, the bracket openings are occluded to prevent the intrusion of adhesive, for example, by using a clip 40 that has a finger that inserts into the opening.

Figure 19:
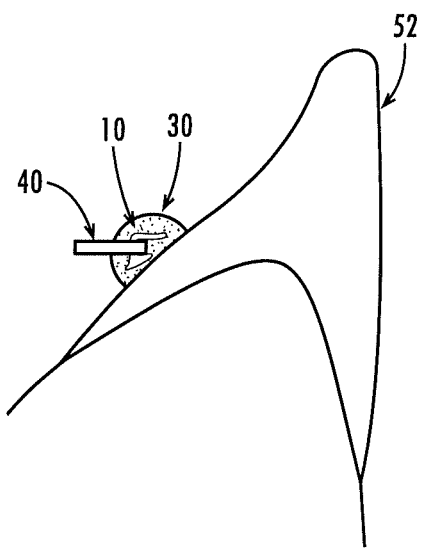
FIG. 19 is a side view of the bracket of FIG. 2 encapsulated and bonded to the model teeth, according to the method of FIG. 18.
Figure 20:
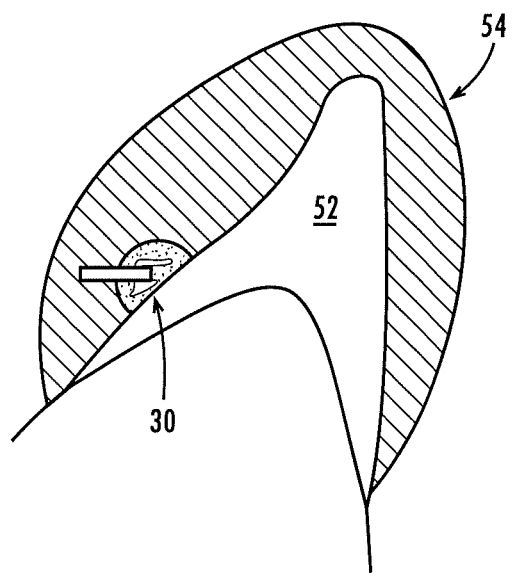
FIG. 20 is a side view of an impression being made of the model teeth, bracket, and encapsulation, according to the method of FIG. 18.
Figure 21:
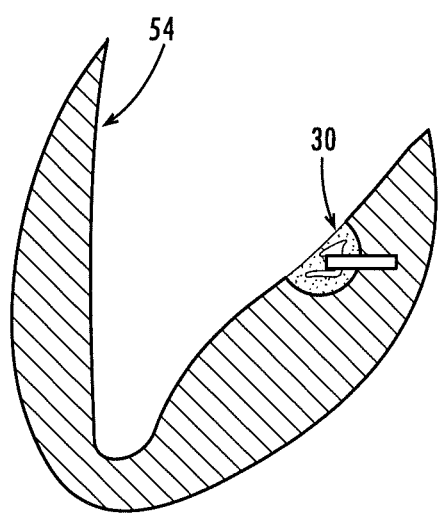
FIG. 21 is a side view of the impression, bracket, and encapsulation removed from the model teeth, according to the method of FIG. 18.

Next, the positioned bracket 10 is encapsulated and bonded to the model teeth 52 with the adhesive 30, as shown in FIG. 19. Then a transfer tray is formed around the clips 40, brackets 10, adhesive encapsulation 30, and model 52 using an impression material 54 such as a thermoplastic material, as shown in FIG. 20. Next, the transfer tray is removed. The mechanical interlocking of the tray impression material around the clips assists in breaking the bond of the adhesive to the model teeth such that the clips 40, the brackets 40, and adhesive 30 encapsulating them are removed from the model and are now contained in the impression material 54 in the tray, as shown in FIG. 21. The operator can assist breaking the bonds of the brackets to the model via insertion of an instrument underneath or through the tray material to mechanically force a breakage.

Figure 22:
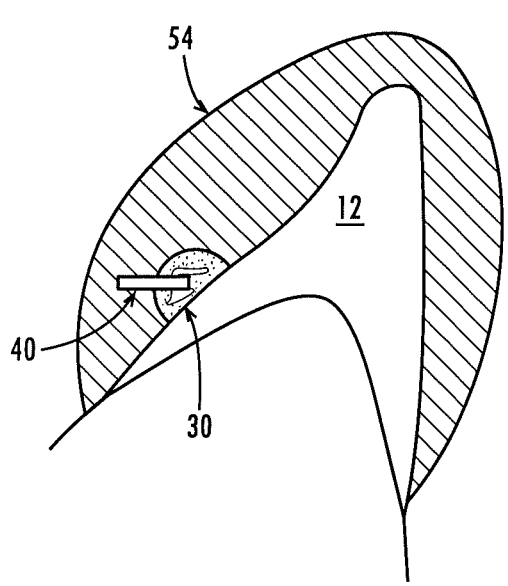
FIG. 22 is a side view of the impression, bracket, and encapsulation positioned on the patient's teeth from which the model teeth were made, according to the method of FIG. 18.
Figure 23:
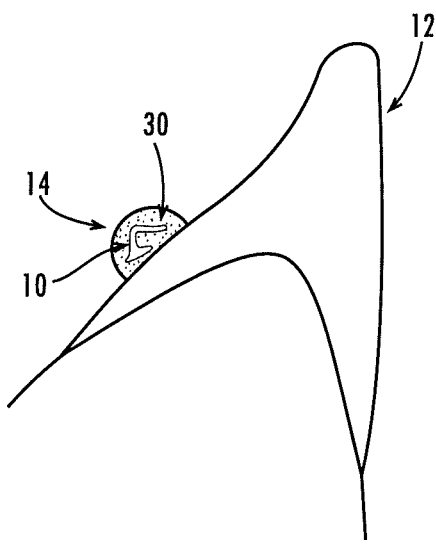
FIG. 23 is a side view of a completed orthodontic attachment with the adhesive material encapsulating the bracket and the opening unobstructed, according to the method of FIG. 18.

Next, the impression material/transfer tray 54, bracket 10, and adhesive encapsulation 30 are positioned on the patient's teeth 12 from which the model teeth 52 were made, as shown in FIG. 22. Then the brackets 10 are bonded to the teeth 12 using an adhesive 30 (prior applied or newly applied), which may be the same or a different type from that used to bond the brackets to the model teeth 52. The impression material/transfer tray 54 is then removed from the teeth 12, leaving the brackets, adhesive mass, and clips bonded to the teeth. The transfer tray impression material 54 can be easily pulled off the brackets 10 by hand. And the bracket openings are unoccluded, for example, by removing the clips, leaving the bracket openings unobstructed and ready to receive the wire through them. FIG. 23 shows a completed orthodontic attachment 14, with the adhesive material 30 encapsulating the bracket 10 and bonded to the tooth, while the opening is unobstructed.

Figure 24:
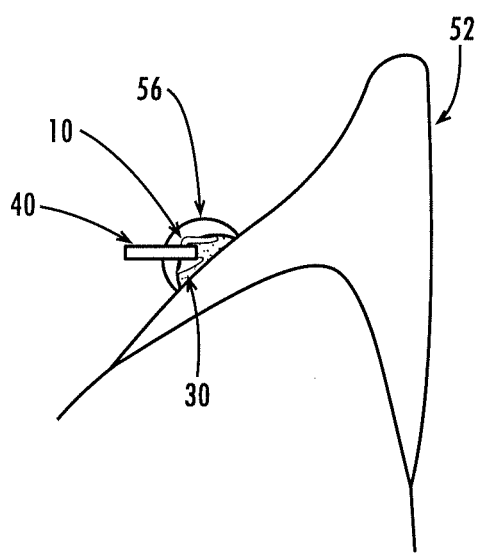
FIG. 24 is a side view of the bracket of FIG. 2 bonded to the model teeth and alternatively encapsulated by being covered with a shell.
Figure 25:
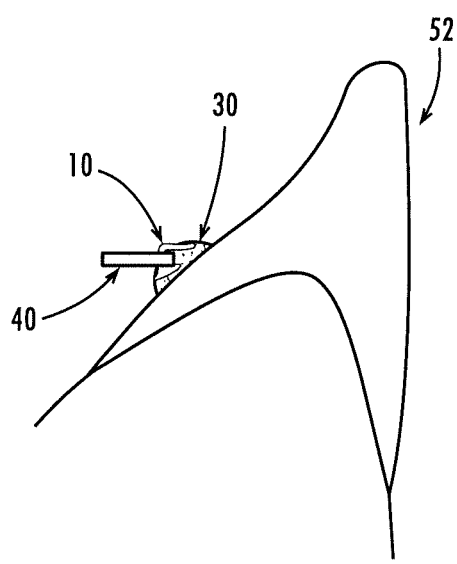
FIG. 25 is a side view of an alternative completed orthodontic attachment with the bracket embedded into but not encapsulated by the adhesive material.

An alternative method of attaching the brackets 10 to teeth 12 to form the attachments 14 and appliances 34 is similar to the exemplary method described above. In this alternative method, however, the brackets 10 are encapsulated by bonding the brackets 10 to the model teeth 52 and, instead of encapsulating them with the adhesive 30, applying removable shells 56 over the brackets, as shown in FIG. 24. The shells 56 may be plastic or made of another material with sufficient rigidity that they do not compress when the impression material is applied to it. Then an impression is made in the impression material of the shell-encapsulated bracket, the impression material and shell-encapsulated bracket are removed from the model teeth, the shell is removed from the impression material, and the void left where the shell was is now filled with the adhesive material. Using this method, the resulting low profile cap over the bracket is very smooth and uniform so to be less noticeable to the user's tongue.

Another alternative method of attaching the brackets 10 to teeth 12 to form the attachments 14 and appliances 34 is similar to the methods described above. In this alternative method, however, the brackets 10 are not encapsulated, but are merely embedded into a mass of the adhesive. In particular, after the bracket 10 is positioned relative to the model teeth 52, a mass of the adhesive 30 is applied to the model teeth and the bracket is embedded into the mass and thereby bonded to the model teeth, as shown in FIG. 24. But the bracket 10 is not covered with the adhesive or otherwise encapsulated. The resulting attachment has a lower profile because no material is applied over the lingual side of the bracket. And because the bracket 10 is embedded in the adhesive 30, that is, the bracket is sunk at least somewhat into the adhesive mass, the resulting bond is strong. Of course, the brackets can be bonded to the teeth with the adhesive only being between the bracket and the tooth, without being encapsulated or embedded into the adhesive, if that is desired in a given case.

Method of Attaching the Brackets to Teeth to Form the Appliance (Method Two)

Turning now to FIGS. 26-56, there is shown a second exemplary method of attaching orthodontic brackets 10 to teeth 12 to form the attachments 14 and the appliance 34. This method is similar to the first exemplary method described above, but uses modified brackets, clips, and transfer trays, and substantial steps of the process are automated. The modifications to the brackets, clips, and transfer trays are described below in the description of the method steps.

In particular, the method includes the following steps:

A. digitally positioning virtual orthodontic brackets and attachments on a virtual model of a patient's teeth;

B. digitally generating a virtual transfer tray for the virtual teeth model and attachments;

C. fabricating a physical transfer tray that is a replica of the virtual transfer tray; and D. bonding the physical attachments onto the physical patient's teeth using the physical transfer tray.

It will be understood that the method may be implemented including all or only a portion of these steps, and that the method may be implemented utilizing devices and articles other than those particularly described herein. The steps will now be described in detail.

It should be pointed out that, as used herein, the term "virtual" means "simulated in electronic form by means of a computer or computer network." In addition, where the terms bracket, attachment, clip, and transfer tray are used herein without the adjectives "virtual" or "physical," the intended meaning is a physical embodiment of the item, not a virtual one.

A. Digitally Positioning Virtual Orthodontic Brackets and Attachments

Figure 26:
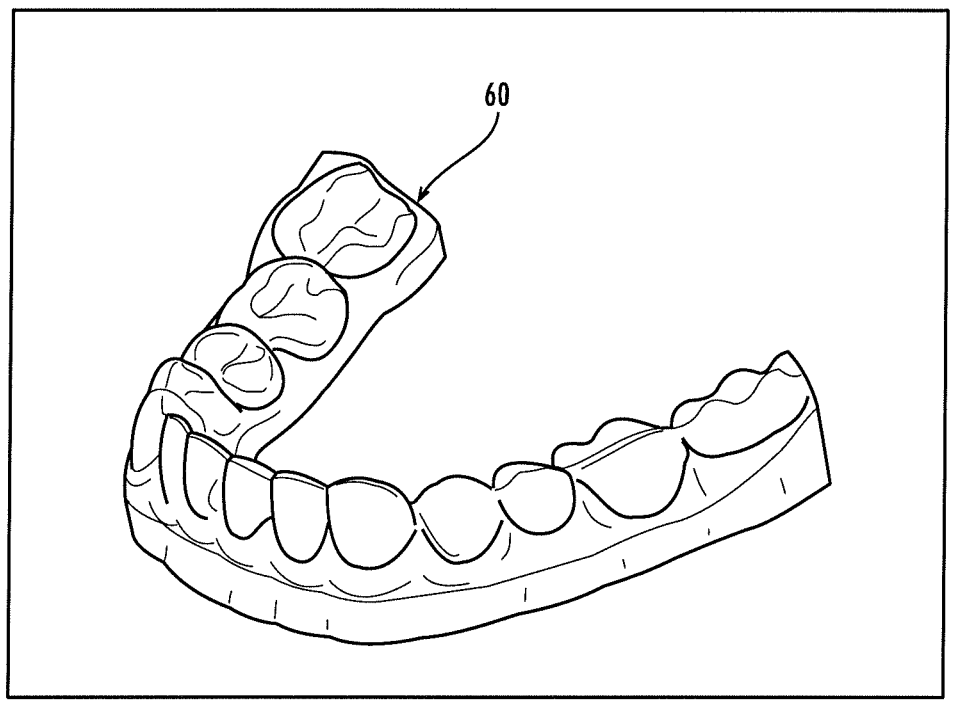
FIG. 26 is a perspective view of a virtual model of a patient's teeth digitally generated according to a second exemplary method of the present invention.

The first step is creating a three-dimensional (3D) digital representation of the patient's teeth. For example, FIG. 26 shows a screen shot of a 3D virtual model 60 the patient's teeth. This step can be done by direct or indirect 3D scanning methods and systems.

In conventional indirect 3D scanning methods, a physical impression of the patient's teeth is made using conventional materials and techniques well known in the art. For example, materials such as alginate or polyvinylsiloxane may be used to make the impression. Next, a physical model is made from the impression using conventional methods and materials well known in the art. For example, materials such as Gypsum stone or plaster may be used to make the model. Then, a conventional digital 3D scanner is used to scan the model and digitally generate the virtual 3D model 60 of the patient's teeth. Alternatively, the impression itself can be scanned, instead of scanning a model made from the impression. The physical impression and model are typically made by the orthodontist and sent to a third party service provider who scans the physical model to create the virtual model 60. Then the service provider stores the virtual model 60 on a computer-readable medium so that it can be accessed by the orthodontist. For example, the virtual model 60 can be stored on a computer server that is connected to the Internet and accessible by the orthodontist, stored on a computer and emailed to the orthodontist, or it can be stored on a CD-ROM or flash memory device that is sent to the orthodontist by overnight delivery. If desired, the orthodontist can acquire a digital 3D scanning system and perform the scanning in his office. One such system and commercially available indirect scanning service is provided by CADENT, Inc. of Or Yehuda, Israel under the brand ORTHOCAD IQ.

In conventional direct 3D scanning methods, the virtual 3D model 60 of the patient's teeth is digitally generated by scanning the teeth directly or "intra-orally." This technique eliminates the need to make the impression of the patient's teeth and the physical model from the impression. Several systems exist for making direct intra-oral scans. One such commercially available system is provided by ORAMETRIX, Inc. of Dallas, Tex. under the brand SURESMILE. This system includes a scanner that requires coating the teeth with a powder to create a more opaque surface for scanning. Another such system has been demonstrated by CADENT, Inc. of Or Yehuda, Israel under the brand ORTHOCAD. This intra-oral scanning system does not require coating the teeth with a powder and thus provides a more efficient scanning process.

Various other systems and devices for digitally creating the 3D virtual model 60 of teeth are disclosed in U.S. Pat. No. 6,099,314; U.S. Pat. App. Pub. No. US2006/0212260; U.S. Pat. App. Pub. No. US2006/0158665; and U.S. Pat. App. Pub. No. US2003/0160784, which are herein incorporated by reference. Various of these and other direct and indirect scanning systems and techniques are suitable for use in the present method, so long as the result is that the 3D virtual model 60 obtained is suitable for use in the subsequent steps.

Referring now to FIGS. 27-35, once the 3D virtual model 60 has been digitally generated, it is rendered into graphical form for display on a computer screen. The next steps are digitally rendering and positioning virtual brackets 62 on the virtual model, digitally rendering the virtual clips 68, digitally generating and rendering virtual attachments 64 including the virtual brackets encapsulated in a virtual adhesive mass 72, and generating and rendering a virtual transfer tray 66 for the virtual attachments. These steps are typically done by the orthodontist in his office using proprietary software stored on a conventional computer having input devices (e.g., keyboard and mouse) and an output device (e.g., a monitor). FIGS. 27-35 are screen shots of the orthodontist's computer display showing the virtual teeth 60, the virtual brackets 62, the virtual clips 68, the virtual adhesive mass 72, the virtual attachments 64, and the virtual transfer tray 66. Details of this proprietary software system are included in co-owned U.S. patent application Ser. No. 11/566,934, filed on Dec. 5, 2006, and titled "SYSTEM AND METHOD FOR POSITIONING ORTHODONTIC BRACKETS ON A VIRTUAL MODEL OF A PATIENT'S TEETH." An overview of the software will now be provided.

The software functions to access and display the virtual model 60 of the patient's teeth, for example, by downloading it from the service provider's server computer, and to digitally generate and display the virtual brackets 62 with openings 70, attachments 64 with adhesive masses 72, transfer trays 66, and clips 68. The virtual brackets 62 with openings 70 and the virtual clips 68 are digital replicas of the corresponding physical ones, which are described in more detail below. And the virtual attachments 64 with adhesive masses 72 and the virtual transfer trays are digitally generated for subsequent use in making the corresponding physical ones, which are described in more detail below. The software includes a variety of novel tools and features for assisting the orthodontist (or other user) in the proper and accurate positioning of the virtual brackets 62. For example, the software preferably functions to display a menu of available sizes and configurations of the virtual brackets 62 and clips 68, and to permit the user to select the desired virtual brackets and clips to be used based on tooth type, size, position, etc.

In a typical commercial embodiment, the software implements one of two different methodologies for determining coordinated positions of the virtual brackets 62 to produce the desired treatment outcome. One methodology is mathematical and the other is a virtual "set-up" methodology.

When implementing the mathematical methodology, the software functions to allow the user to select points, lines, or planes on the surface anatomy of each virtual tooth in the model 60, with each point, line, or plane representing a particular aspect the tooth anatomy. In addition, the software functions to allow the user to designate the value of certain angular or linear units of measure. The software then uses this information to determine the spatial position of the virtual bracket 62 for that virtual tooth. As an example, the user could select two points on each tooth of the virtual model 60 that represent the mesial and distal interproximal contact points of the tooth. The software then determines a particular orientation for each virtual bracket 62 on each tooth so that the virtual bracket opening 70 parallels the lines formed by these selected points, and displays each virtual bracket in the determined position on the virtual teeth 60. As another example, the user could select a point, line, or plane, that represents the location of the cusp tip (or incisal edge if an incisor) of a tooth. In addition, the user can input a linear distance and vector from this point, line, or plane. The software then determines the "vertical" position of the virtual bracket 62 relative to the point, line, or plane. The software preferably functions to allow the user to select the point, line, or plane by clicking on displayed points, lines, and/or planes, or by plotting/drawing the point, line, or plane on the virtual model 60.

When implementing the virtual "set-up" methodology, the software functions to allow the user to digitally manipulate each virtual tooth of the virtual model 60 from its initial mal-aligned position to a position corresponding to the desired outcome of the treatment. The software functions to then allow the user to position the virtual brackets 62 on the well-aligned virtual teeth in an orientation such that a virtual non-deflected arch-wire in one plane (or segments of wire that simulate the arch shape) can pass through each of the virtual bracket openings 70. The position of each of the virtual brackets 62 relative to the corresponding virtual tooth 60 is digitally retained, while the software returns the virtual teeth to their original mal-aligned positions in the original virtual model. The software now displays the virtual model 60 of mal-aligned teeth with each virtual bracket 62 in its proper position.

Alternatively, the software can implement a combination of these two methodologies to predict the outcome of treatment, and hence, the proper positioning of the virtual brackets 62. The user can use the mathematical component to initially position the virtual brackets 62. Then the software virtually rearranges the virtual teeth 60 based on the initial position of each virtual bracket 62. The user can then identify flaws in the mathematical prediction and make adjustments using the virtual "set-up" component. It will be understood that other positioning methodologies can be implemented by the software.

Figure 27:
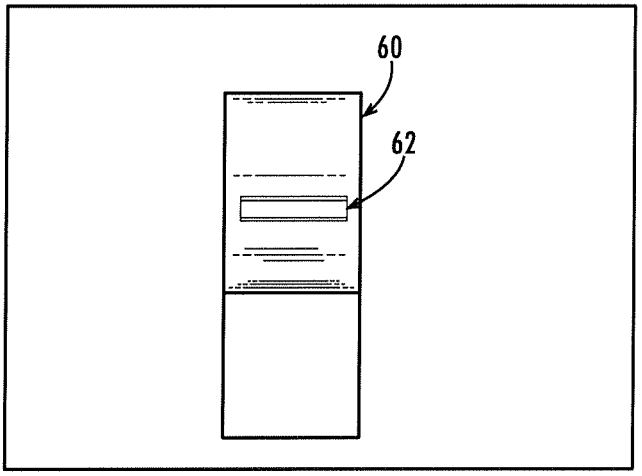
FIG. 27 is a rear (lingual) view of one of the virtual teeth of FIG. 26, showing a virtual bracket being positioned offset from the virtual tooth (and thus suspended in free space) according to the second exemplary method, with the tooth shown in an "extruded" cross-section for simplification.
Figure 28:
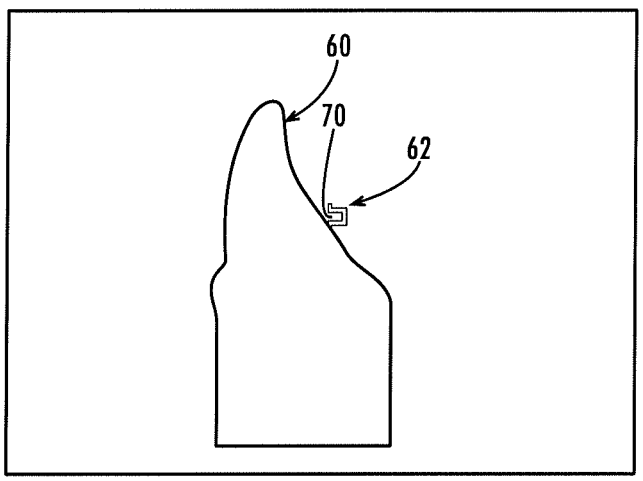
FIG. 28 is a left side view of the virtual tooth and bracket of FIG. 27.
Figure 29:
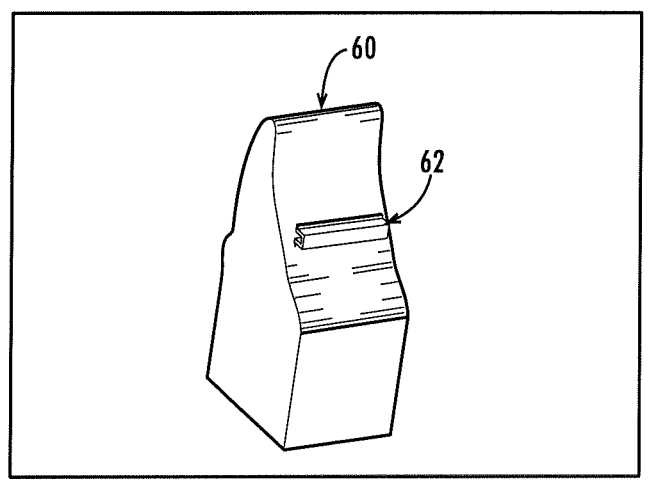
FIG. 29 is a perspective view of the virtual tooth and bracket of FIG. 27.

Regardless of the particular methodology implemented, the software functions to allow the user to reference relevant anatomical features of the virtual teeth to determine their desired position and coordinate the position with adjacent virtual brackets, to manipulate the virtual brackets 62 with six degrees of freedom but with no part of the virtual brackets forming a lever arm against the virtual teeth 60, to position the virtual brackets suspended in free space (offset from or adjacent to the lingual or facial surfaces of the virtual teeth), and to display the virtual model of mal-aligned teeth with each virtual bracket in its proper position. FIGS. 27-29 show one of the virtual brackets 62 positioned relative to one of the virtual teeth 60, with the tooth shown in an "extruded" cross-section for simplification. These virtual brackets 62 are virtual replicas of the physical brackets 10 described in detail herein.

Figure 30:
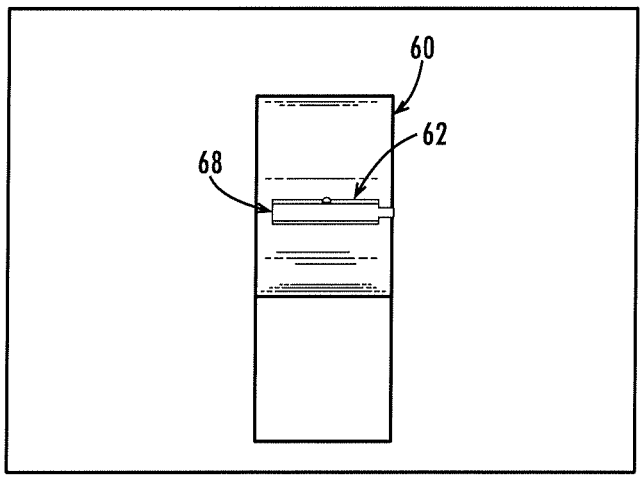
FIG. 30 is a rear (lingual) view of the virtual tooth and bracket of FIG. 27, showing a virtual clip added to the virtual bracket according to the second exemplary method.
Figure 31:
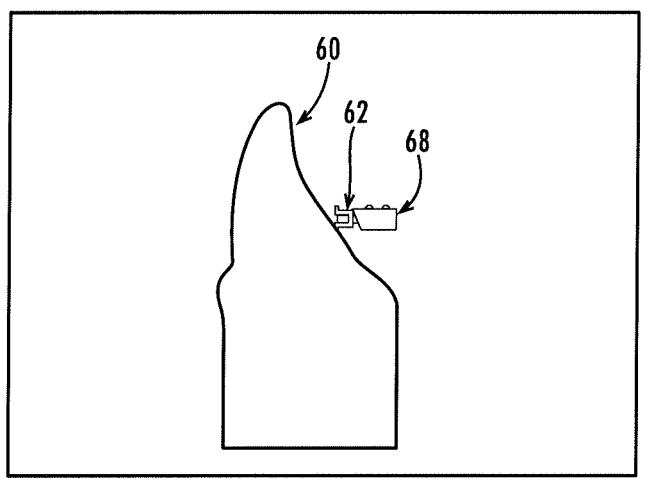
FIG. 31 is a left side view of the virtual tooth, bracket, and clip of FIG. 30.
Figure 32:
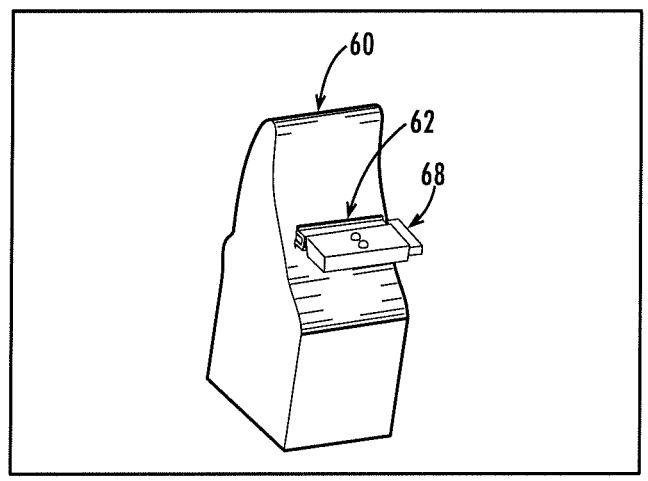
FIG. 32 is a perspective view of the virtual tooth, bracket, and clip of FIG. 30.

Once the virtual brackets 62 are positioned relative to the virtual teeth 60, the software functions to allow the user to add virtual occlusions to the bracket openings 70, for example, by using the virtual clips 68 that have a finger that inserts into the opening. As mentioned above, the software preferably displays a menu of available clip types, sizes, and configurations for the user to select from. FIGS. 30-32 show one of the virtual clips 68 digitally slid onto one of the virtual brackets 62 on the virtual teeth 60, with the tooth shown in an "extruded" cross-section for simplification. The virtual clips 68 are virtual replicas of the physical clips 40 that engage the physical brackets 10 to assist in the process of transferring the physical attachments 14 to the physical teeth 12 of the patient.

Figure 33:
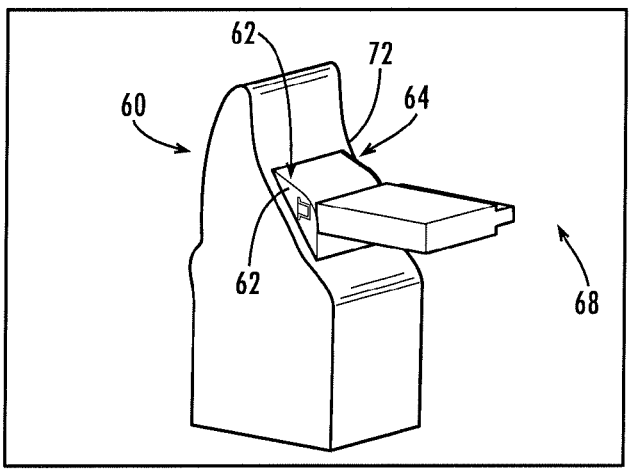
FIG. 33 is a perspective view of the virtual tooth, bracket, and clip of FIG. 32, showing a virtual adhesive mass added to form a virtual attachment according to the second exemplary method.

Once the virtual brackets 62 and clips 68 are in position, the software functions to allow the user to automatically or manually add the virtual adhesive mass 72 for encapsulating or embedding the virtual attachments 64. FIG. 33 shows one of the virtual attachments 64 on one of the virtual teeth 60, with the virtual bracket 62 offset from the tooth and thus suspended in free space. The virtual tooth 60 and the virtual adhesive mass 72 of FIG. 33 are shown in an "extruded" cross-section for simplification—the virtual adhesive mass has a smoother contour than us depicted.

B. Digitally Generating the Virtual Transfer Tray

Figure 34:
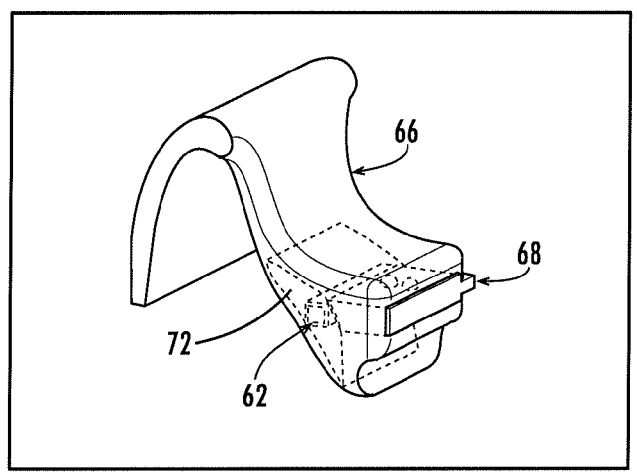
FIG. 34 is a perspective view of a section of a virtual transfer tray digitally generated based on the virtual attachment, clip, and tooth of FIG. 33 according to the second exemplary method.
Figure 35:
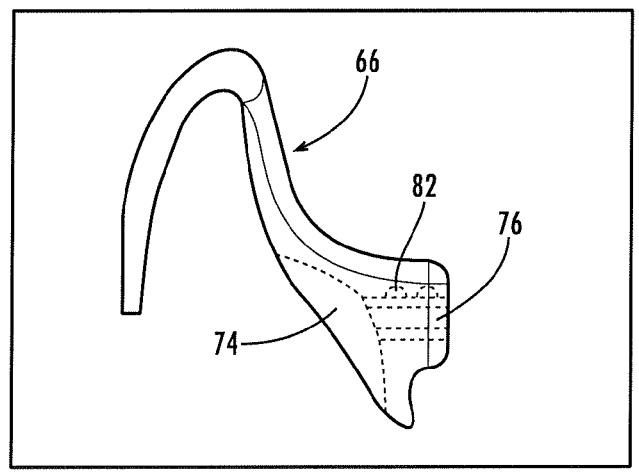
FIG. 35 is a left side view of the virtual transfer tray section of FIG. 34.

Referring now to FIGS. 34 and 35, in the next step the software digitally generates the virtual transfer tray 66 based on the unique geometry of the virtual teeth 60 and the particular shape and selected positions of the virtual attachments 64 and clips 68. The virtual transfer tray 66 is generated with a void 74 for receiving the virtual adhesive mass 72 and bracket 62, and with a slot 76 for receiving the virtual clip 68. The software generates the void 74 with a size, shape, and position for later producing a physical adhesive mass that will provide good strength and a smooth contour for patient comfort. Thus, preferably the void 74 is generally dome-shaped. The software generates the slot 76 with a size, shape, and position so that it holds the virtual clip 68 in the position needed to hold the virtual bracket 62 in the selected position suspended in free space and offset from the virtual tooth 60. Details of the void, the slot, orientation features, and undercut management of the virtual transfer tray 66 are provided below in the description of the physical transfer tray, which is a replica of the virtual one. In addition, the software preferably includes novel tools and features that permit the user to modify the design of the virtual transfer tray 66.

C. Fabricating the Physical Transfer Tray

In the next step of the method, a physical transfer tray 54 is made that is a physical replica of the virtual transfer tray 66. The physical transfer tray 54 is made to hold the physical brackets 10, adhesive mass 30, and clips 40, and to fit them onto the physical teeth 12. It will be understood that, as used herein, the term "clip" refers to any occluding element that functions as described herein, including structures that are not clip-like, such as plugs or bars. Before describing the fabrication of the physical transfer tray 54, some structural details of the physical clips 40, brackets 10, and transfer tray will be provided.

Referring now to FIGS. 36-41, the physical clips 40, brackets 10, and transfer tray 54 are similar to those described above and shown in FIGS. 15-17, 2-10, and FIGS. 20-22, respectively, but with a few modifications. It will be understood that preferable results are achieved by the method when using the physical clips 40, brackets 10, and transfer tray 54 described herein, but that other types of these items could be used with the method to obtain desirable benefits.

Figure 36:
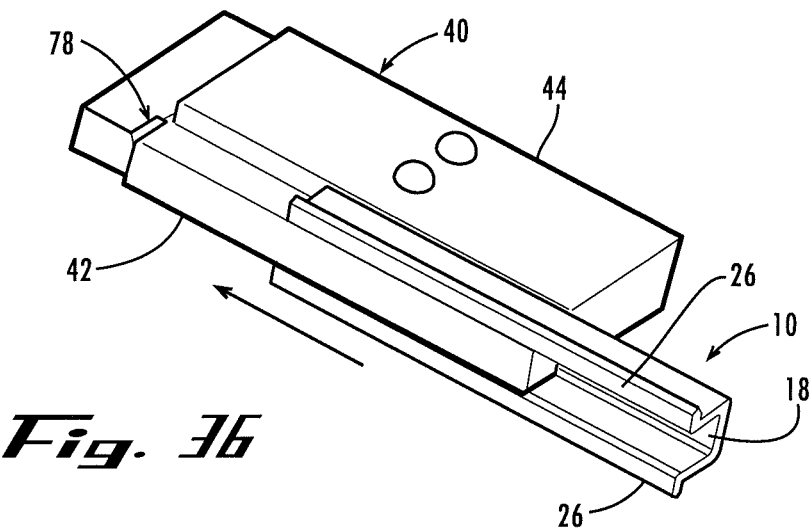
FIG. 36 is a perspective view of a physical clip and bracket, for which the virtual clip and bracket of FIGS. 30-31 are virtual replicas, for use according to the second exemplary method.
Figure 37:
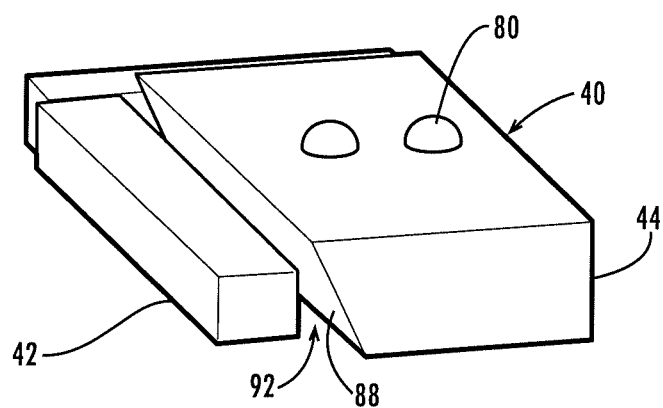
FIG. 37 is a perspective view of the physical clip of FIG. 36.
Figure 38:
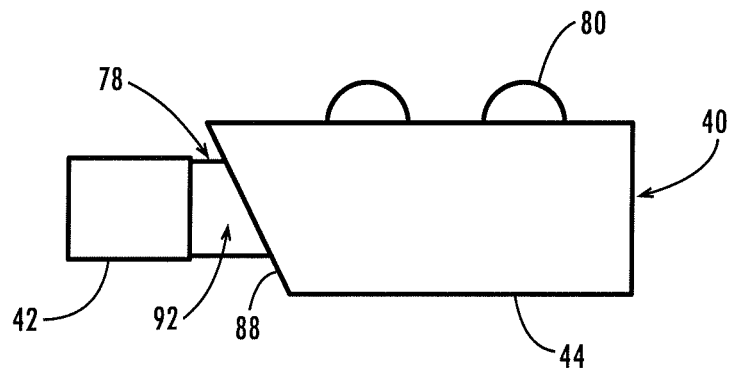
FIG. 38 is a right side view of the physical clip of FIG. 36.

As shown in FIG. 36, each of the physical brackets 10 similarly has a body 16 with an opening 18 for receiving the wire in it and with retention flanges 26 for distributing forces over a larger area of the adhesive. The physical bracket 10 does not have a flat (or other-shaped) base with a broad surface area for bonding directly to the tooth and fixing the position of the opening, as do conventional orthodontic brackets. Instead, the physical bracket 10 can be positioned in free space with the opening 18 at a customized, pre-selected angle relative to the tooth surface, and can be oriented with six degrees of freedom, without any part of the body 16 creating a lever arm against the tooth surface. In this way, the physical bracket 10 can be oriented in a wide range of positions while maintaining a low profile and low visibility. Somewhat differently from the embodiments shown in FIGS. 5A-5E, the physical bracket 10 depicted in FIG. 36 is similar to that shown in FIGS. 5F-5I in that it has more-uniformly thick walls and a more-rectangular shape so that it can be used on a wider range of tooth types and positions.

As shown in FIGS. 36-39, each of the physical clips 40 similarly has a finger 42 that it is received in the physical bracket opening 18 and a handle portion 44 for grasping. To prevent the adhesive 30 from intruding into and occluding the opening (and thus to prevent or hinder later routing the wire through the opening), the finger 42 has a length that is equal to or greater than the length of the physical bracket opening 18 (the finger extends all the way through the opening) and the finger has a cross-sectional shape generally conforming to that of the bracket opening 18 (at least it does at the two ends of the bracket opening). Somewhat differently from the earlier-described embodiments, the physical clip 40 depicted here has a reduced-strength zone 78 between the finger 42 and the handle 44 that fails when the finger is subjected to a shearing force, so that the finger breaks away from the handle (see also FIG. 52). For example, the reduced-strength zone 78 may be provided by a circumferential channel or a notch in the finger.

Figure 39:
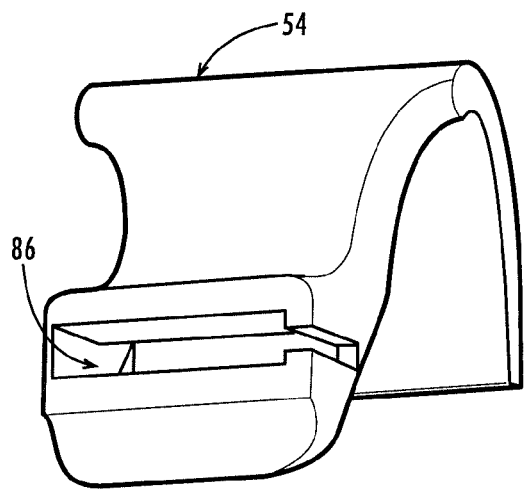
FIG. 39 is a perspective view of a section of a physical transfer tray fabricated to be a physical replica of the virtual transfer tray of FIGS. 34 and 35 according to the second exemplary method.
Figure 40:
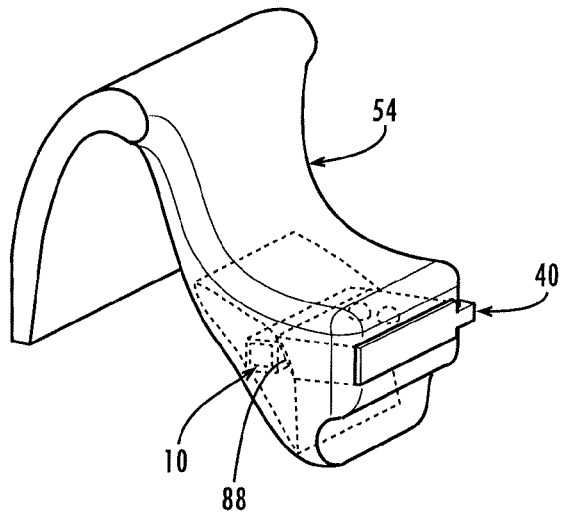
FIG. 40 is a rear perspective view of the physical transfer tray section of FIG. 39, showing the physical clip and bracket of FIG. 36 added according to the second exemplary method.
Figure 41:
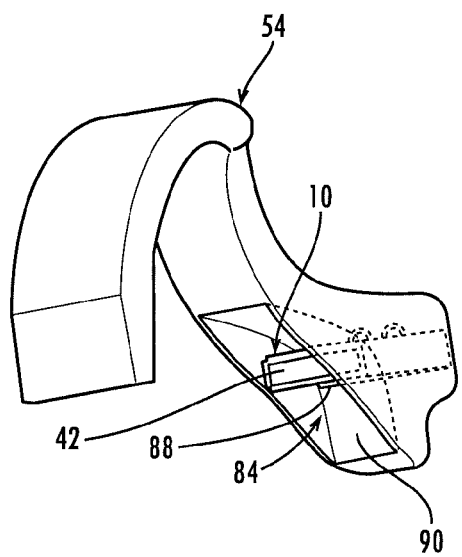
FIG. 41 is a front perspective view of the physical transfer tray section of FIG. 40.
Figure 42:
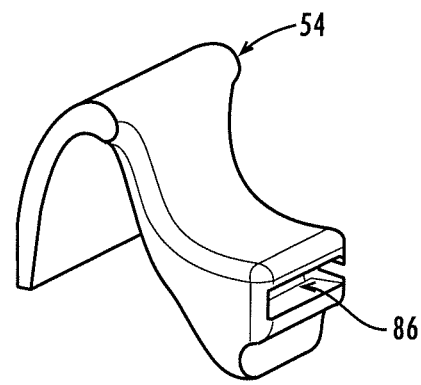
FIG. 42 is a rear perspective view of the physical transfer tray section of FIGS. 39-41 ready to receive the physical clip and bracket of FIG. 36.
Figure 43:
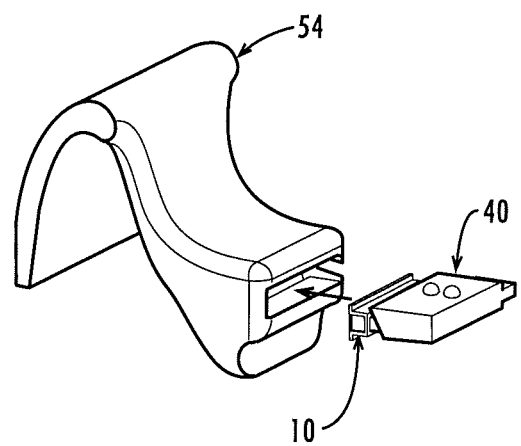
FIG. 43 is a rear perspective view of the physical transfer tray section of FIG. 42, showing the bracket and clip of FIG. 36 being inserted into a slot in the transfer tray according to the second exemplary method.
Figure 44:
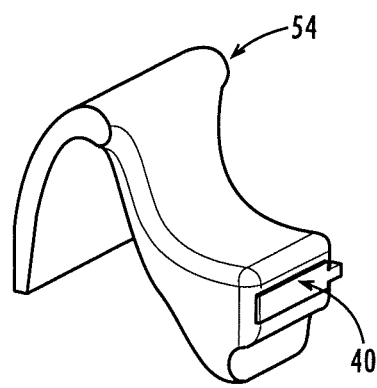
FIG. 44 is a rear perspective view of the physical transfer tray section, clip and, bracket of FIG. 43, showing the bracket and clip snapped into place in the transfer tray slot to properly position the bracket according to the second exemplary method.

FIGS. 39-41 show details of the physical transfer tray 54, and for simplification depicts only a segment of the tray for holding one bracket. The depicted transfer tray segment is for a bottom arch of teeth, and a similar transfer tray for the top teeth is made in the same fashion with the only difference (other than the customized positions of the voids, slots, and attachment elements, as discussed below) being that it is inverted. The physical transfer tray 54 is preferably made of a translucent plastic, as described below, though other materials can be used.

In addition, the physical transfer tray 54 is designed to accommodate undercut areas in its inner surface. For example, the tray material can be selected for having some resiliency to provide a limited degree of deflection, or the software can be programmed to design the tray without tray material in undercut areas or with a thinner wall in undercut areas to allow greater deflection of the tray. If the tray material is too rigid, the transfer tray may not deflect outward to get around a protruding area of a tooth to fit into an undercut underneath the protrusion. Current "undercut strategy" in the fabrication of a physical transfer tray is limited to either blocking out recessed undercut areas on the teeth model prior to fabricating the transfer tray or eliminating protruding undercut areas on the tray after fabrication. For practical reasons, working in the physical realm greatly limits the scope of any undercut strategy. However, fabrication of the transfer tray in the virtual realm allows the opportunity to control the location and degree of undercut engagement, and the shape and thickness of the material that will bend to engage the undercut. The shape and thickness of the tray can be optimized to produce a tray that will flex in the most favorable way without breaking (i.e. elastic deformation). A virtual tray can be designed with undercuts in strategic locations while undercuts in other areas (e.g., where there is severe mal-alignment) are completely eliminated.

Furthermore, the virtual transfer tray 54 can be digitally generated with novel features that are not generally practical to incorporate in typical transfer trays made from teeth impressions. One feature is that the virtual tray can be provided with holes strategically placed anywhere the operator identifies as a region where there might be a defect in the virtual teeth model. In this way, the operator avoids later creating a physical tray with a bulge that would prevent fully seating the physical tray on the physical teeth. Another feature is that the virtual tray can be provided with holes strategically placed in the tray to expose the tips of teeth. In this way, when the operator later seats the physical tray on the physical teeth, the operator can easily see the penetration of the teeth tips through the holes and thus verify that the tray is fully seated.

Because the physical transfer tray 54 is a physical replica of the virtual transfer tray 66, it has voids 84 for receiving the physical adhesive masses 72 and brackets 10, and slots 86 for receiving the physical clips 40 with a snap fit. For teeth that are to have only a single bracket 10, the voids 84 and slots 86 are provided in the transfer tray 54 in a one-to-one relationship with the teeth, and for any teeth that will have two brackets there are two voids and slots for those teeth.

In the depicted embodiment, the segments of the transfer tray 54 have a continuous facial (outer/front) wall while the lingual (inner/rear) wall defines partial gaps. So when a series of the depicted segments are formed together, the completed transfer tray 54 has a continuous facial wall and a "scalloped" lingual wall with gaps between sections of the wall where the voids 84 and slots 86 are. In this way, the transfer tray 54 is more flexible, which makes it easier to put on and take off of the teeth, and the slots 86 have at least one open side through which part of the clip extends, which makes it easier to move the bracket/clip 10/40 assemblies into and out of the slots. In addition, the teeth are mal-aligned at the start of the treatment program, and the voids 86 and slots 86 are custom-oriented relative to the mal-aligned teeth, so the transfer tray 54 is custom-made with the void-defining wall sections mal-aligned relative to the smooth arch desired at the conclusion of the treatment. In an alternative embodiment, the transfer tray has a continuous lingual wall.

Referring to FIGS. 37-41, the interrelationships between the physical clip 40 and the physical transfer tray 54 will now be described. The physical clip 40 includes attachment elements 80 that engage mating attachment elements 82 of the physical transfer tray 54 to hold the clip, and thus the bracket 10, in the precise position determined in the bracket-positioning step. The attachment elements 80 and 82 may be detents, male and female dimples, or other conventional structures that cooperate to provide a snap fit between two parts. Preferably, the size and shape of the slot 86 are selected (by the proprietary software discussed above) to generally conform to the size and shape of the clip 40 with the clip being slightly smaller so that the clip is held in place but can be readily inserted into and removed from the slot. To facilitate inserting and removing the clip 40 from the slot 86, they are tapered from larger at the lingual side of the transfer tray to smaller at the void 84. In addition, the void 84 is formed into the inner surface of the physical transfer tray 54, and the slot 86 extends through the tray from the void to the outer surface of the tray. To prevent the encapsulating adhesive mass 30 from being forced out of the void 84 and into the slot 86 in the latter step of bonding the attachments 14 to the teeth 12, the physical clip 40 has a mold surface 88. When the physical clip 40 is inserted into the slot, the mold surface 88 extends substantially across the slot where it meets the void, thereby cooperating with the void-defining inner surface 90 of the tray to form a continuous, smooth, dome-like surface. In the depicted the physical clip 40, there is a gap 92 between the finger 42 and the mold surface 88, and the mold surface is angled from vertical, which makes this embodiment well-suited for lingual placement.

As mentioned above, for different teeth sizes (e.g., youths, adults) and types (e.g., molars, incisors), different sizes and types of the brackets 10 may be provided. To accommodate different sizes or shapes of bracket openings 18, correspondingly different sizes or shapes of clips 40 are also provided, which may in some case also require the transfer trays 54 to be designed (using the above-described proprietary software) with correspondingly different sizes of slots 86. Thus, in practice the orthodontist may keep in the office (or order on a case-by-case basis) a kit with a variety of different brackets 10 and clips 40.

Having described details of the structure of the physical transfer tray 54, details of the step of fabricating it will now be described. As discussed above, the user (i.e., an orthodontist working in his/her office) first accesses (e.g., downloads via the Internet) data representing the virtual model 60 of the patient's teeth or generates the data on-site, and then uses the software to digitally manipulate the data to position the virtual brackets 62 and to digitally generate the virtual transfer tray 66. The orthodontist then sends (e.g., via the Internet) the data representing the virtual transfer tray 66 to a third party service bureau or centralized facility at a remote location where the data is used to fabricate the physical transfer tray 54 out of a plastic or other suitable material. The physical transfer tray 54 is then sent (e.g., via overnight delivery) to the orthodontist's office for use. Alternatively, the fabrication of the physical transfer tray 54 can be done on-site at the orthodontist's office.

In one aspect of the method of the invention, the physical transfer tray 54 is fabricated by a conventional rapid prototyping machine. Rapid prototyping is a group of technologies that enable manufacturers and designers to fabricate parts without the need for expensive and time-consuming production molds. Rapid prototyping, sometimes referred to as layered manufacturing or rapid manufacturing, takes a computer file of a part, slices it into layers, and fabricates each layer one-at-a-time, stacking the layers until a complete 3D prototype is made. The advantages include that parts can be seen, felt, and tested before committing to expensive and time-consuming production molds. Thus, rapid prototyping is conventionally used to more-efficiently create and test prototype parts, not to fabricate production parts. The use of rapid prototyping in the present method is a novel application in several ways. First of all, it is used to produce custom physical orthodontic transfer trays 54 that are unique to each individual. Second, no physical mold is needed to make the physical transfer trays 54. Third, for indirect bonding, it eliminates the need for a precision placement machine (e.g., a robot) for placing the physical brackets 10, and it eliminates several other steps involved in the bracket positioning such as temporary bonding, fabricating an RTV transfer tray, and applying a clear RTV layer to the tray to allow for light curing. And fourth, the rapid-prototyped physical transfer trays 54 serve as a means of custom-positioning the orthodontic brackets 10 in the ideal anatomical location for optimal tooth repositioning unique to each individual's anatomy. That is, instead of using a manual or robotic bracket-placement system, the customized position of each bracket 10 is designed into the rapid-prototyped transfer tray 54, which stores the precise location of the brackets relative to the individual's specific tooth anatomy without the brackets actually touching the teeth. Various rapid prototyping methods and apparatus are disclosed in U.S. Pat. Nos. 7,128,866; 6,261,077; 6,159,411; 6,146,487; and 6,110,409, which are herein incorporated by reference.

D. Bonding the Physical Attachments onto the Physical Patient's Teeth

Now that the physical transfer tray 54 has been fabricated, it must be prepared for use. The orthodontist or other user first assembles the physical brackets 10 onto the physical clips 40 (see FIG. 36). Then the user grasps (manually or with a tool) the handles 44 of the clips 440 and inserts the physical bracket/clip assemblies 10/40 into the slots 86 of the physical transfer tray 54 (see FIGS. 42-44). Because of the cooperating attachment elements 80 and 82 of the clips 40 and the tray 54, the bracket/clip assemblies 10/40 are held in the precise position set when using the software to design and generate the virtual transfer tray, with the bracket suspended in free space within the void 84 (see FIGS. 40 and 41). As such, the spatial orientation of the bracket 10 is not dependent on the tooth's surface anatomy. Alternatively, these transfer tray preparation steps may be done by another party such as the third party service bureau who fabricates the physical transfer tray 54.

Figure 45:
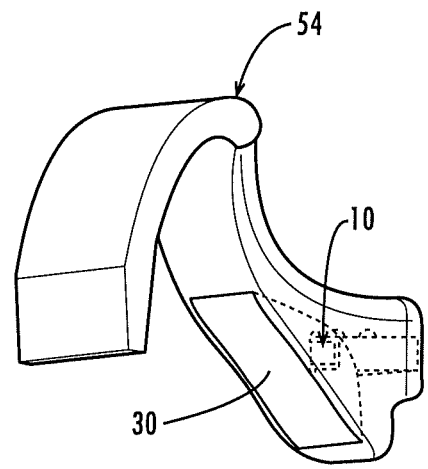
FIG. 45 is a front perspective view of the physical transfer tray section of FIG. 44, showing an adhesive mass added into a void in the tray according to the second exemplary method.
Figure 46:
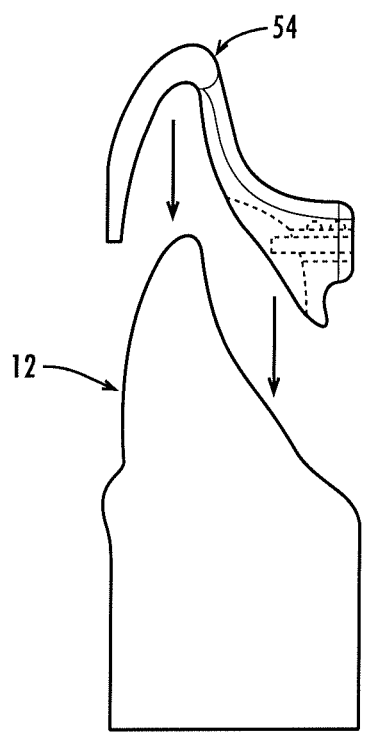
FIG. 46 is a side view of the physical transfer tray section, holding the physical bracket, clip, and adhesive mass of FIG. 45, being placed onto one of the patient's physical teeth (which the virtual teeth are replicas of) according to the second exemplary method.
Figure 47:
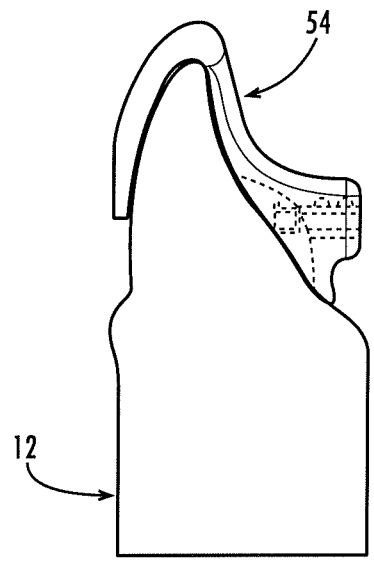
FIG. 47 is a side view of the physical transfer tray section, bracket, clip, and adhesive mass of FIG. 46, seated on the patient's physical teeth according to the second exemplary method.

Referring to FIG. 45, in the next step the orthodontist or other user fills each void 84 of the physical transfer tray 54 with the adhesive (e.g., a light-cured, composite resin) until it encapsulates the bracket 10, which remains held precisely in position in the void by one of the clips 40. The voids 84 preferably are not filled with the adhesive until the patient is in the orthodontist's office to have the orthodontic attachments 14 put on. Preferably, the voids 84 in the tray 54 are over-filled with adhesive to ensure a complete bond to the tooth 12 and complete formation of the domed adhesive mass 30, which is defined by the dome-shaped void-defining inner tray surface 90 and the mold surface 88 of the clip 40. Depending on the particular adhesive used, the teeth 12 may need to be prepared as prescribed by the provider of adhesive.

Figure 48:
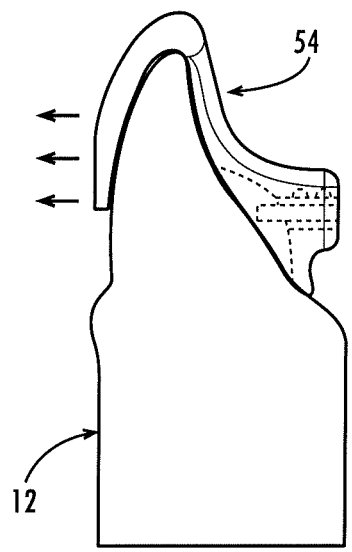
FIG. 48 is a side view of the physical transfer tray section of FIG. 45 deflecting slightly as it is placed on the tooth.
Figure 49:
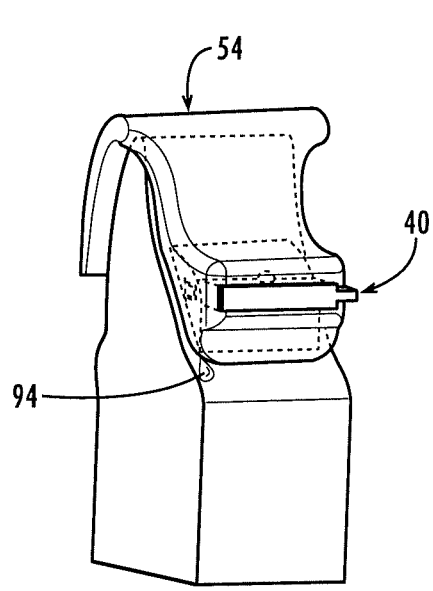
FIG. 49 is a rear (lingual) view of the physical transfer tray section, bracket, clip, and adhesive mass seated on the tooth of FIG. 47, showing excess adhesive mass squeezed from the transfer tray void.

Referring to FIGS. 46-49, the orthodontist or other user then seats the prepared physical transfer tray 54 onto the patient's physical teeth 12. As shown in FIG. 48, if there are any undercut areas on the transfer tray 54 that could prevent proper seating on the teeth, the tray will deflect (see the directional arrows) to accommodate the undercut areas. As shown in FIG. 49, because the void 84 was overfilled, the excess adhesive 94 will "ooze" out from the tray 54, and the user can then remove this excess adhesive 94 before curing.

Figure 50:
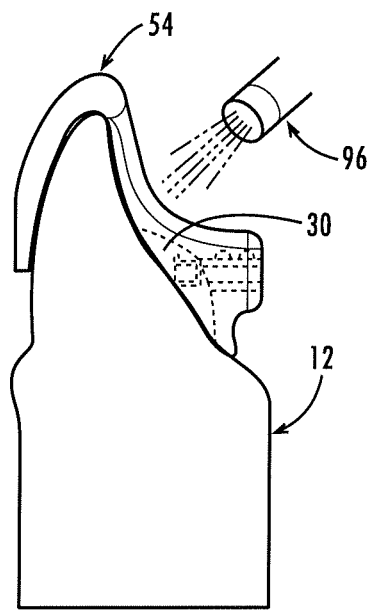
FIG. 50 is a side view of the physical transfer tray section, bracket, clip, and adhesive mass seated on the tooth of FIG. 47, showing the adhesive mass being light-cured so that it bonds to the tooth according to the second exemplary method.

Referring to FIG. 50, the adhesive mass 30 is then cured so that it bonds to the tooth 12. For example, when using a conventional dental, light-cured, composite resin adhesive and a translucent transfer tray, the adhesive mass 30 is cured by using a light source (e.g., a conventional dental blue light-emitting diode). The blue LED is used to direct the blue light 96 through the translucent tray 54 and onto the adhesive mass 30 to cure it. Of course, other types of adhesives can be used, and accordingly other types of curing methods can be used.

Figures 51, 53:
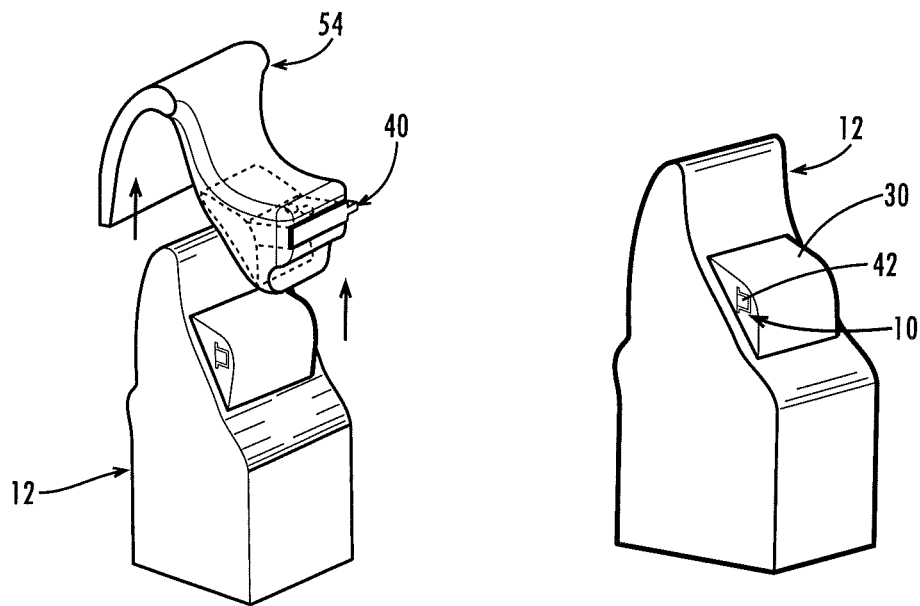
FIG. 51 is a perspective view of the physical transfer tray section being removed from the tooth of FIG. 50 according to the second exemplary method.
FIG. 53 is a perspective view of the physical adhesive mass, bracket, and broken-off clip finger of FIG. 50 remaining on the tooth after the transfer tray section has been removed from the tooth according to the second exemplary method.
Figure 52:
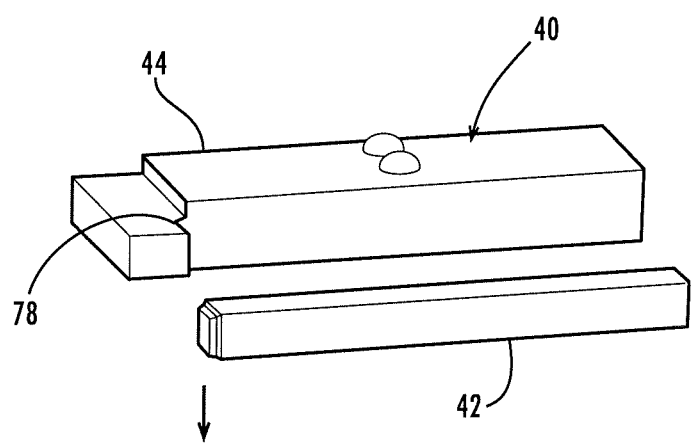
FIG. 52 is a perspective view of the physical clip, showing the clip finger breaking away when the physical transfer tray is removed from the tooth of FIG. 50 according to the second exemplary method.

The next step in the method is to remove the transfer tray 54 from the teeth 12. As shown in FIG. 51, the user pulls the transfer tray 54 off of the teeth 12. As shown in FIG. 52, this imparts a shearing force on the fingers 42 of each of the clips 40 (because the fingers are still in the openings 18 of the brackets 10 of the attachments 14, which are now bonded to the teeth 12), thereby causing the reduced-strength zones 78 to fail so that all of the fingers break off. In an alternative embodiment, a release mechanism is built into the tray design that allows the entire clip to break out of the bottom of the tray. As shown in FIG. 53, this leaves only the attachments 14 (with the fingers 42 still in the openings 18 of the brackets 10 of the attachments), which do not pull away from the teeth 12 with the transfer tray 54 because the adhesive masses 30 have been bonded to the teeth. If there are any undercut areas on the transfer tray 54 that could prevent or hinder removal of the transfer tray 54, the tray will deflect to accommodate this (see again FIG. 48). It should be noted that the adhesive mass 30 as depicted is generally semi-cylindrical for ease of illustration, but in practice it is preferably dome-shaped with a smooth contour.

Figures 54, 55:
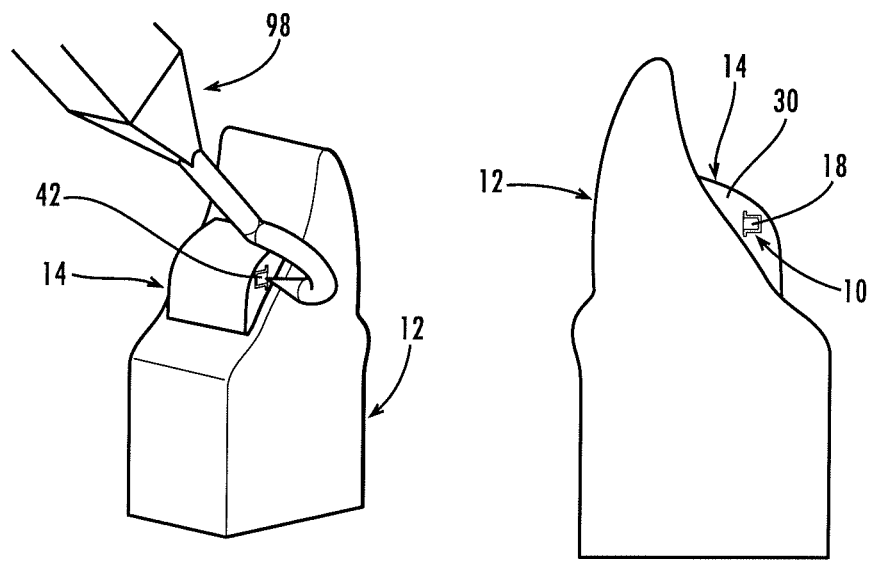
FIG. 54 is a perspective view of the physical adhesive mass, bracket, and broken-off clip finger of FIG. 54, showing the broken-off clip finger being removed from the bracket opening according to the second exemplary method.
FIG. 55 is a side view of the physical adhesive mass and bracket of FIG. 54, with the broken-off clip finger removed to form a physical attachment according to the second exemplary method.

The next step is to remove the fingers 42 from the openings 18 of the brackets 10 of the attachments 14. This can be done by pushing out the fingers 42 using a conventional dental tool 98, as shown in FIG. 54. This leaves only the attachments 14 (the brackets 10 encapsulated in the adhesive mass 30) on the teeth 12, as shown in FIG. 55, with the bracket opening 18 unobstructed throughout its length.

Figure 56:
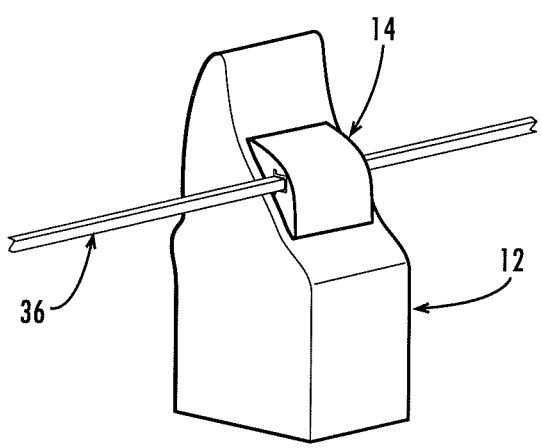
FIG. 56 is a perspective view of the physical attachment of FIG. 54, showing a wire being routed through the bracket opening to form the physical appliance of FIGS. 11-14 according to the second exemplary method.

As shown in FIG. 56, the final step is to thread the wire 36 through the openings 18 in the brackets 10 to form the completed appliance 34 (see FIGS. 11-14). In the depicted embodiment, a straight rectangular wire 36 is inserted into the rectangular opening 18 of a single bracket 10 on a single tooth 12. At the beginning of the orthodontic treatment program, adjacent teeth 12 are mal-aligned and so their brackets 10 are also mal-aligned. As such, the first wire 36 inserted is typically a small cross-section, round, highly flexible, highly resilient wire capable of large deflection that imparts a comparably low force upon this large degree of deflection (these qualities are found in conventional orthodontic wires made of nickel-titanium alloys and copper-nickel-titanium alloys, among others). Later in the treatment program, rectangular, larger-diameter wires may be installed, as needed for the desired treatment outcome.

In an alternative method of the invention, the brackets engage (e.g., by snapping) directly with attachment elements formed in the transfer tray, and the bracket openings are occluded by plugs or other occlusion elements for keeping the adhesive out of the bracket openings, thereby eliminating the need for the clip. For example, attachment elements (e.g., male dimples) can be designed into the transfer tray using the proprietary software so that the dimples engage attachment elements (e.g., female dimples) of the bracket, thereby holding the bracket in the transfer tray.

In another aspect of the invention, these attachment elements are designed to both hold the bracket and to occlude the bracket openings. For example, attachment elements (e.g., rectangular male dimples) can be designed into the transfer tray using the proprietary software so that the dimples snap into both open ends of the rectangular bracket opening, thereby orienting and holding the bracket in the transfer tray and at the same time occluding the bracket opening. As another example, a small section of flat wire made of SLA may be suspended across each of the voids in the transfer tray, from one side of the void to the other, where the bracket opening needs to be. Then one of the brackets is slid onto each wire to both hold the brackets in place and occlude the bracket openings from filling with the adhesive.

In yet another aspect, the invention includes a kit with the items described herein for use with the method described herein. In this aspect, the invention includes a kit with a number of the brackets and clips.

In view of the foregoing, it will be appreciated that various aspects of the present invention provide advantages over conventional orthodontic brackets, attachments, appliances, and methods of orthodontic treatment using these elements. These advantages include, but are not limited to, the provision of a base-independent bracket system that eliminates the lever-arm effect and thereby allows for effectively unlimited customization of bracket opening orientation while maintaining the lowest possible attachment profile.

In addition, the innovative bracket system and positioning method eliminates the need for an open-faced slot in the attachments and instead provides a bracket that is used to form an attachment with a close-faced opening. Therefore, no tie wings and thus no ligature ties are needed, so the brackets have a lower profile and are smoother. Furthermore, because a closed-faced system possesses limitations on the degree of wire bends that can be placed, this then requires a high degree of precision positioning of the attachments to minimize the need for such bends and thus to minimize the need for manual adjustments by the operator and thus provide for much more efficient and less costly treatment and less stress for doctor, and reduced treatment time. Moreover, the lack of tie-wings and ligature ties allows for far less friction which permits more efficient translation of forces to teeth, which in turn permits easier sliding, which results in higher efficiency.

Furthermore, aspects of the present invention provide for precise coordination of over-lapping wire segments to create a "simulated-continuous" wire system. This overcomes the problem of needing a large wire bend at the canine-premolar in the traditional lingual methods—therefore, one creates a useable straight-wire system on the lingual side with a minimal bracket profile height and maximum smoothness. For example, the first premolar could receive two attachments (or one double-opening attachment) on the lingual side to serve as the overlap point for creating the simulated continuous wire mechanical system. This permits the use of straight wire segments exclusively—theoretically an entire arch could be composed of multiple two-tooth segments that alternate between facial and lingual (or they could be all on the lingual or all on the facial using a double-opening attachment). In addition, this permits using anterior attachments on the lingual side of anterior teeth and posterior attachments on the facial side of posterior teeth, with one tooth on each side being the point of overlap and having both a facial and lingual attachment. Furthermore, this permits the use of different horizontal planes for each wire segment—one can be placed higher, the other lower.

Moreover, the anterior lingual application of the attachments provides additional advantages. The anterior attachments can be placed on the lingual side of the teeth to keep them out of sight. The small profile of the attachments maintains patient comfort. And the smooth surface of the encapsulated attachments further enhances patient comfort. Finally, an appliance including the lingual and facial attachments of the size, shape, and position as proposed can be maintained in place following active therapy to serve as a semi-permanent fixed retainer. This type of fixed retainer would be unique in that the wire can be removed while leaving the attachments in place. As such, the wire can be removed to facilitate cleaning by the patient and can be replaced with a new or the same wire. This type of fixed retainer would also be unique in that the same appliance serves as both the treatment mechanism and the retainer mechanism. This eliminates the need for fabrication of an additional retainer appliance at the completion of active therapy. Furthermore, any fixed retainer has the advantage of not requiring compliance by the patient (unlike a removable retainer that requires the patient remember to wear it) and the advantage of being more comfortable and attractive than removable appliances that are visible on the facial side and generally quite bulky.

It is to be understood that this invention is not limited to the specific devices, methods, conditions, and/or parameters described and/or shown herein, and that the terminology used herein is for the purpose of describing particular embodiments by way of example only. Thus, the terminology is intended to be broadly construed and is not intended to be limiting of the claimed invention. In addition, as used in the specification including the appended claims, the singular forms "a," "an," and "the" include the plural, plural forms include the singular, and reference to a particular numerical value includes at least that particular value, unless the context clearly dictates otherwise. Furthermore, any methods described herein are not intended to be limited to the sequence of steps described but can be carried out in other sequences, unless expressly stated otherwise herein.

Moreover, while certain embodiments are described above with particularity, these should not be construed as limitations on the scope of the invention. It should be understood, therefore, that the foregoing relates only to exemplary embodiments of the present invention, and that numerous changes may be made therein without departing from the spirit and scope of the invention as defined by the following claims.

The invention claimed is:

1. A method of forming an orthodontic transfer tray for use in attaching orthodontic brackets to teeth, the brackets each having an opening for receiving a wire, the method comprising:
    positioning the brackets relative to the teeth, or to a model of the teeth, with at least one of the brackets offset from the teeth or the teeth model and thereby suspended in free space;
    defining customized surfaces that form customized voids that receive the brackets in customized positions such that at least one of the voids can receive a respective adhesive mass that fills a remainder of the void so that the respective offset bracket is embedded into or encapsulated by the adhesive mass with the adhesive mass extending into the void beyond at least a portion of the respective bracket opening but not into the bracket opening; and
    fabricating the transfer tray including the customized surfaces forming the customized voids for holding the brackets in their customized positions relative to the teeth, wherein the fabricated transfer tray can have the voids loaded with the brackets, occlusion elements occluding the bracket openings, and the adhesive masses, and can then be placed on the teeth so that the brackets are in the customized positions with at least one of the adhesive masses extending away from the respective tooth beyond the respective bracket-opening portion of the respective offset bracket but with the respective occlusion element preventing the respective adhesive mass from flowing into the respective bracket opening.

2. The method of claim 1, wherein:
    the step of positioning the brackets comprises digitally positioning virtual brackets relative to virtual teeth of a 3D virtual model of the teeth, wherein the virtual brackets are virtual replicas of the brackets;

the step of defining customized surfaces comprises digitally generating a virtual transfer tray including virtual voids, wherein the virtual voids are virtual replicas of the voids; and the step of fabricating the transfer tray comprises fabricating the transfer tray to be a physical replica of the virtual transfer tray.

3. The method of claim 2, wherein the 3D virtual model of the teeth is formed by a direct method including scanning the teeth intra-orally or by an indirect method including forming an impression of the teeth and then either digitally scanning the impression of the teeth or forming a 3D physical model of the teeth using the impression and digitally scanning the physical model of the teeth.

4. The method of claim 2, wherein the step of fabricating the transfer tray further comprises using a rapid prototyping system to fabricate the transfer tray.

5. The method of claim 1, wherein the step of positioning the brackets further comprises manipulating the brackets with six degrees of freedom and with no part of the brackets acting as a lever arm against the teeth or the teeth model.

6. The method of claim 1, wherein the occlusion elements are provided by clips with fingers that insert into and thereby occlude the bracket openings.

7. The method of claim 6, wherein the step of fabricating the transfer tray further comprises fabricating the transfer tray with an outer surface defining customized slots for receiving the clips therethrough so that the clips can be extended into the voids through the slots and, with the brackets mounted onto the clips with the clips inserted into the bracket openings, the brackets are suspended within the voids.

8. The method of claim 1, wherein the step of fabricating the transfer tray further comprises fabricating the transfer tray with first attachment elements that mate with second attachment elements to register the brackets in their respective positions.

9. The method of claim 8, wherein the second attachment elements are formed on the occlusion elements.

10. A method of forming an orthodontic transfer tray for use in attaching orthodontic brackets to teeth, the brackets each having an opening for receiving a wire, the method comprising:

digitally positioning virtual brackets relative to virtual teeth of a 3D virtual model of the teeth, wherein the virtual brackets are virtual replicas of the brackets, wherein at least one of the virtual brackets is offset from the virtual teeth and thereby suspended in virtual free space;

digitally defining customized surfaces that form virtual customized voids that receive the virtual brackets in customized positions such that when the transfer tray is fabricated with customized voids that are physical replicas of the virtual customized voids then one of the voids receives the respective offset bracket and a respective adhesive mass that fills a remainder of the void so that the offset bracket is embedded into or encapsulated by the adhesive mass with the adhesive mass extending into the void beyond at least a portion of the respective bracket opening but not filling the bracket opening;

digitally generating a virtual transfer tray including the virtual voids for holding the virtual brackets in the customized positions relative to the virtual teeth; and fabricating the transfer tray with the customized voids for holding the brackets in their customized positions relative to the teeth, wherein the transfer tray with the customized voids is a physical replica of the virtual transfer tray with the virtual customized voids, wherein the voids can be loaded with the brackets, occlusion elements occluding the bracket openings, and the adhesive masses, and the fabricated transfer tray can then be placed on the teeth so that the brackets are in the customized positions with at least one of the adhesive masses extending away from the respective tooth beyond but the respective bracket-opening portion of the respective offset bracket but with the respective occlusion element preventing the respective adhesive mass from flowing into the respective bracket opening.

11. The method of claim 10, wherein the 3D virtual model of the teeth is formed by a direct method including scanning the teeth intra-orally or by an indirect method including forming an impression of the teeth and then either digitally scanning the impression of the teeth or forming a 3D physical model of the teeth using the impression and digitally scanning the physical model of the teeth.

12. The method of claim 10, wherein the step of fabricating the transfer tray further comprises using a rapid prototyping system to fabricate the transfer tray.

13. The method of claim 10, wherein the step of digitally positioning the virtual brackets further comprises digitally manipulating the virtual brackets with six degrees of freedom and with no part of the virtual brackets acting as a virtual lever arm against the virtual teeth.

14. The method of claim 10, further comprising the step of digitally occluding the virtual bracket openings with virtual occlusion elements, wherein the virtual occlusion elements are virtual replicas of occlusion elements used to attach the brackets to the teeth, wherein the step of digitally defining virtual customized surfaces that form virtual customized voids comprises defining virtual customized voids that receive the virtual brackets in customized positions such that at least one of the virtual voids can receive a respective virtual adhesive mass that fills a remainder of the respective virtual void so that the respective virtual offset bracket is embedded into or encapsulated by the virtual adhesive mass with the virtual adhesive mass extending into the virtual void beyond at least a portion of the respective virtual bracket opening but with the respective virtual occlusion element preventing the virtual adhesive mass from filling the bracket opening.

15. The method of claim 14, wherein the occlusion elements are provided by clips with fingers that are receivable in and occlude the bracket openings.

16. The method of claim 14, wherein the step of fabricating the transfer tray further comprises fabricating the transfer tray with an outer surface defining customized slots for receiving the occlusion elements therethrough so that the occlusion elements can be extended into the voids through the slots and, with the brackets mounted onto the occlusion elements with the occlusion elements inserted into the bracket openings, the brackets are suspended within the voids.

17. The method of claim 10, wherein the step of fabricating the transfer tray further comprises fabricating the transfer tray with an outer surface defining customized slots for receiving therethrough occlusion elements so that the occlusion elements can be extended into the voids through the slots and, with the brackets mounted onto the occlusion elements with the occlusion elements inserted into the bracket openings, the brackets are suspended within the voids and the bracket openings are occluded to prevent the adhesive masses from flowing thereinto.

18. The method of claim 10, wherein the step of digitally generating the virtual transfer tray comprises digitally generating the virtual transfer tray with first virtual attachment elements that register the virtual brackets in their respective positions.

19. The method of claim 10, wherein the step of fabricating the transfer tray further comprises fabricating the transfer tray with first attachment elements that mate with second attachment elements to register the brackets in their respective positions.

* * * * *